(12) United States Patent
Vaillancourt et al.

(10) Patent No.: US 6,683,181 B2
(45) Date of Patent: Jan. 27, 2004

(54) PYRROLOQUINOLONES AS ANTIVIRAL AGENTS

(75) Inventors: Valerie A. Vaillancourt, Kalamazoo, MI (US); Sandra Staley, Kalamazoo, MI (US); Audris Huang, Irvine, CA (US); Richard Allen Nugent, Galesburg, MI (US); Ke Chen, Kalamazoo, MI (US); Sajiv K. Nair, Portage, MI (US); James A. Nieman, Galesburg, MI (US); Joseph Walter Strohbach, Mendon, MI (US)

(73) Assignee: Pharmacia and Upjohn Comapny, Kalamazoo, MI (US)

( * ) Notice: Subject to any disclaimer, the term of this patent is extended or adjusted under 35 U.S.C. 154(b) by 0 days.

(21) Appl. No.: 10/288,117

(22) Filed: Nov. 5, 2002

(65) Prior Publication Data

US 2003/0153561 A1 Aug. 14, 2003

Related U.S. Application Data

(62) Division of application No. 09/888,283, filed on Jun. 22, 2001, now Pat. No. 6,525,049.
(60) Provisional application No. 60/215,986, filed on Jul. 5, 2000, and provisional application No. 60/277,012, filed on Mar. 19, 2001.

(51) Int. Cl.⁷ .................... C07D 295/03; C07D 211/06; C07D 207/04; C07D 211/23
(52) U.S. Cl. ................... 544/178; 544/59; 544/60; 544/82; 544/106; 544/121; 544/126; 544/358; 544/404; 546/94; 546/184; 548/400; 548/950; 564/509
(58) Field of Search ............... 544/59, 106, 358, 544/178, 60, 82, 121, 126, 404; 546/184, 94; 548/400, 950; 564/509

(56) References Cited

U.S. PATENT DOCUMENTS

| | | | |
|---|---|---|---|
| 3,917,609 A | 11/1975 | Gerster | 260/287 P |
| 4,317,820 A | 3/1982 | Ishikawa et al. | 424/246 |
| 4,547,511 A | 10/1985 | Eriksoo et al. | 514/312 |
| 5,026,856 A | 6/1991 | Yatsunami et al. | 546/156 |
| 5,792,774 A | 8/1998 | Haughan et al. | 514/294 |
| 5,935,952 A | 8/1999 | Todo et al. | 514/230.2 |

FOREIGN PATENT DOCUMENTS

| | | | |
|---|---|---|---|
| GB | 2236751 A | | 4/1991 |
| JP | 55145612 | | 11/1980 |
| JP | 55153792 | | 11/1980 |
| WO | WO91/05783 | | 5/1991 |
| WO | WO92/18483 | | 10/1992 |
| WO | WO97/30999 | | 8/1997 |
| WO | WO97/31000 | | 8/1997 |
| WO | WO99/32450 | | 7/1999 |
| WO | WO 00/05218 | * | 2/2000 |
| WO | WO00/40561 | | 7/2000 |

OTHER PUBLICATIONS

Kano H et al. J, Med. Chem. (1967) 10(3), 411–18.*
Blurton, Peter, et. al. "Palladium Catalysed Coupling of Iodoquinolines and Acetylenes—A novel Entry to the Pyrrolo[3,2,1—ij]– Quinoline Nucleus." *Heterocycles*. vol. 45, No. 12, pp. 2395–2403, 1997.

* cited by examiner

Primary Examiner—Evelyn Mei Huang
(74) Attorney, Agent, or Firm—Lucy X. Yang; Jonthan P. O'Brien

(57) ABSTRACT

The present invention provides a compound of formula I

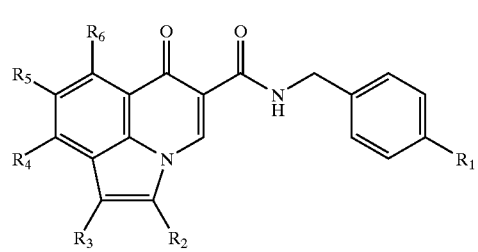

which is useful as antiviral agents, in particular, as agents against viruses of the herpes family.

7 Claims, No Drawings

PYRROLOQUINOLONES AS ANTIVIRAL AGENTS

This is a division of application U.S. Ser. No. 09/888,283, filed Jun. 22, 2001 U.S. Pat. No. 6,525,044 which claims priority under 35 USC 119(e)(i) to U.S. Ser. Nos. 60/215,986 and 60/277,012, filed Jul. 5, 2000, and Mar. 19, 2001, respectively.

CROSS REFERENCE

This application claims the benefit of the following provisional applications: U.S. Ser. No. 60/215,986, filed Jul. 5, 2000 and U.S. Ser. No. 60/277,012, filed Mar. 19, 2001 under 35 USC 119(e)(i).

FIELD OF THE INVENTION

The present invention provides pyrroloquinolones that are useful as antiviral agents, more specifically, provides compounds of formula (I) described herein below against herpesviruses.

BACKGROUND OF THE INVENTION

The herpesviruses comprise a large family of double stranded DNA viruses. They are also a source of the most common viral illnesses in man. Eight of the herpesviruses, herpes simplex virus types 1 and 2 (HSV-1 and HSV-2), varicella zoster virus (VZV), human cytomegalovirus (HCMV), Epstein-Barr virus (EBV), and human herpesviruses 6, 7, and 8 (HHV-6, HHV-7, and HHV-8), have been shown to infect humans. HSV-1 and HSV-2 cause herpetic lesions on the lips and genitals, respectively.

They also occasionally cause infections of the eye and encephalitis. HCMV causes birth defects in infants and a variety of diseases in immunocompromised patients such as retinitis, pneumonia, and gastrointestinal disease. VZV is the causitive agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

Due to the unique position of the substitutent on the N-phenylmethyl of formula I described herein below, compounds of the present invention demonstrate unexpected activity against the above reference herpesviral infections, particularly, human cytomegaloviral infection.

INFORMATION DISCLOSURE

PCT publication WO 97/31000 discloses pyrroloquinolone carboxamides useful as antiviral agents.

PCT publication WO 97/30999 discloses pyrroloquinolones with bicyclic carboxamides useful as antiviral agents.

U.S. Pat. No. 3,917,609 discloses pyrroloquinoline carboxylic acid derivatives useful as antiviral agents.

U.S. Pat. No. 4,547,511 discloses heterocyclic carboxamides which increase the activity of the immune system.

U.S. Pat. No. 4,317,820 discloses O-lactam series compound useful as antibacterial agents.

U.S. Pat. No. 5,792,774 discloses quinolones and their therapeutic use.

PCT publication WO 91/05783 discloses heterocyclic compounds that are 5-HT$_3$ antagonists.

PCT publication WO 92/18483 discloses quinoline derivatives.

Abstract of Japanese patent J55145-612 discloses antimicrobial agent contains a novel β-lactam ring.

Abstract of Japanese patent J55153-792 discloses cephalosporanic derivatives.

GB 2236751 A discloses 4-oxo-quinolines which are 5-HT3 antagonists.

Blurton, et. al *Heterocycles*, 1997, 45, 2395 discloses the preparation of pyrroloquinolones.

SUMMARY OF THE INVENTION

The present invention provides a compound of formula I,

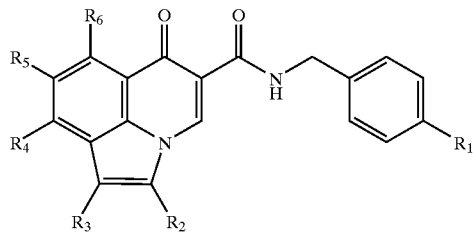

or a pharmaceutically acceptable salt, racemate, solvate, tautomer, optical isomer or prodrug derivative thereof wherein:

$R^1$ is F, Cl, Br, CN or $NO_2$;

$R^2$ and $R^3$ are independently H, halo, $OR^{11}$, $C(=O)R^7$, $C(=O)OR^{11}$, $C_{3-8}$cycloalkyl, $C_{1-7}$alkyl which may be partially unsaturated and optionally substituted by one or more halo, $C_{3-8}$cycloalkyl, $R^2$, $OR^{14}$, $SR^{11}$, $SR^{14}$, $NR^8R^9$, $NR^{11}C(O)R^7$, $(C=O)C_{1-7}$ alkyl, or $SO_mR^{10}$;

$R^4$ and $R^5$ are independently (a) H, (b) halo, (c) aryl, (d) $S(O)_mR^7$, (e) $(C=O)R^7$, (f) $(C=O)OR^{10}$, (g) CN, (h) het, wherein said het is bound via a carbon atom, (i) $OR^{11}$, (j) Ohet, (k) $NR^8R^9$ (l) $SR^{11}$, (m) Shet, (n) $NHCOR^{13}$, (O)$NHSO_2R^{13}$, (p) $C_{3-8}$cycloalkyl, or (q) $C_{1-7}$alkyl which may be partially unsaturated and optionally substituted by one or more $R^{12}$, $OR^{14}$, $SR^{11}$, $SR^{14}$, $NR^8R^9$, halo, $C_{3-8}$cycloalkyl, $(C=O)C_{1-7}$alkyl, or $SO_mR^{10}$;

R is H, halo, $C_{3-8}$cycloalkyl, or $C_{1-4}$alkyl optionally substituted by 1–3 halo;

$R^7$ is (a) $C_{1-7}$alkyl, (b) $C_{3-8}$cycloalkyl, (c) $NR^8R^9$, (d) aryl, or (e) het, wherein said het is bonded via a carbon atom;

$R^8$ and $R^9$ are independently (a) H, (b) aryl, (c) $C_{3-8}$cycloalkyl, (d) $C_{1-7}$alkyl which may be partially unsaturated and is optionally substituted by one or more $NR^{11}R^{11}$, $R^{12}$, $SO_mR^{10}$, $CONR^{11}R^{11}$, OH, aryl, het, $C_{3-8}$cycloalkyl, or halo, or (e) $R^8$ and $R^9$ together with the nitrogen to which they are attached for a het;

$R^{10}$ is (a) aryl, (b) het, (c) $C_{3-8}$cycloalkyl, or (d) $C_{1-7}$alkyl which may be partially unsaturated and is optionally substituted by one or more $NR^{11}R^{11}$, $R^{12}$, SH, $CONR^{11}R^{11}$, $C_{3-8}$cycloalkyl, or halo;

$R^{11}$ is (a) H, (b) $C_{3-8}$cycloalkyl, (c) $C_{1-7}$alkyl optionally substituted by OH, or (d) aryl;

$R^{12}$ is (a) $OR^{11}$, (b) Ohet, (c) Oaryl, (d) $CO_2R^{11}$, (e) het, (f) aryl, or (g) CN;

$R^{13}$ is (a) H, (b) het, (c) aryl, (d) $C_{3-8}$cycloalkyl, or (e) $C_{1-7}$alkyl optionally substituted by $NR^{11}R^{11}$ or $R^{12}$;

$R^{14}$ is (a) $(P=O)(OR^{15})_2$, (b) $CO(CH_2)_nCON(CH_3)-(CH_2)_nSO_3^-M^+$, (c) an amino acid, (d) C(=O)aryl, (e) C(=O)$C_{1-7}$alkyl optionally substituted by $NR^{11}R^{11}$, aryl, het, $CO_2H$, or $O(CH_2)_nCO_2R^{15}$;

$R^{15}$ is (a) H, or (b) $C_{1-7}$alkyl;

aryl is a phenyl radical or an ortho-fused bicyclic carbocyclic radical wherein at least one ring is aromatic; at each occurrence, aryl may be additionally substituted with one or more halo, CN, $CO_2R^{11}$, $SR^{11}$, $OR^{11}$, $NR^{11}R^{11}$, $C_{1-4}$alkyl, $CF_3$, or $C_{3-8}$cycloalkyl;

het is a four—(4), five—(5), six—(6), or seven—(7) membered saturated or unsaturated heterocyclic ring having 1, 2, or 3 heteroatoms selected from the group consisting of O, $SO_m$, and NX; wherein X is H, $C_{1-4}$alkyl or absence, wherein het is optionally fused to a benzene ring, or any bicyclic heterocycle group; at each occurrence, het may be additionally substituted with one or more halo, CN, $CO_2R^{11}$, $COR^{13}$, $SR^{11}$, $OR^{11}$, $NR^{11}R^{11}$, $C_{1-4}$alkyl, $CF_3$, $C_{3-8}$cycloalkyl, oxo or oxime;

at each occurrence, $C_{3-8}$cycloalkyl may be partially unsaturated and optionally substituted by one or more $R^{12}$, $SR^{11}$, $NR^{11}R^{11}$, $CONR^{11}R^{11}$, or halo;

m is 0, 1, or 2; and at each occurrence n is independently 1, 2, 3, 4, 5 or 6;

M is sodium, potassium, or lithium.

The present invention further provides a pharmaceutical composition comprising a compound of formula I, or a pharmaceutically acceptable salt thereof, and a pharmaceutically acceptable carrier (the composition preferably comprises an effective antiviral amount of the compound or salt).

The present invention further provides a method of treating or preventing a herpesviral infection, comprising administering to a mammal in need of such treatment, a compound of formula (I) or a pharmaceutically acceptable salt thereof.

The present invention further provides a method of treating or preventing a herpesviral infection comprising administering orally, parenterally, topically, rectally, nasally, sublingually or transdermally an effective amount of a compound of claim 1.

The present invention further provides a compound of formula (I) or a pharmaceutically acceptable salt thereof for use in medical treatment.

The present invention further provides the use of a compound of formula (I) or a pharmaceutically acceptable salt thereof to prepare a medicament for treating or preventing a herpesviral infection in a mammal.

The present invention further provides a method for inhibiting a viral DNA polymerase, comprising contacting (in vitro or in vivo) the polymerase with an effective inhibitory amount of a compound of formula I, or a pharmaceutically acceptable salt thereof.

The invention also provides novel intermediates and processes disclosed herein that are useful for preparing compounds of formula I.

DETAILED DESCRIPTION OF THE INVENTION

The following definitions are used, unless otherwise described. Halo denotes fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $(C_{1-3})$alkyl refers to alkyl of one to three carbon atoms, inclusive, or methyl, ethyl, propyl and isopropyl, straight and branched forms thereof.

Aryl is a phenyl radical or an ortho-fused bicyclic carbocyclic radical wherein at least one ring is aromatic. Aryl is optionally substituted with one or more substituents selected from the group consisting of halo, CN, $CO_2R_{11}$, $SR_{11}$, $OR_{11}$, $NR_{11}R_{11}$, $C_{1-4}$alkyl, $CF_3$, or $C_{3-8}$cycloalkyl. Preferably, aryl is phenyl, or naphthalene.

Het is a four—(4), five—(5), six—(6), or seven—(7) membered saturated or unsaturated heterocyclic ring having 1, 2, or 3 heteroatoms selected from the group consisting of oxygen (O), sulfur ($S_m$, m is 0, 1, or 2), and nitrogen (NX wherein X is H, $C_{1-4}$alkyl or absence), which is optionally fused to a benzene ring, or any bicyclic heterocycle group. Het is optionally substituted with one or more substituents selected from the group consisting of halo, CN, $CO_2R_{11}$, $COR^{13}$, $SR_{11}$, $OR_{11}$, $NR_{11}R_{11}$, $C_{1-4}$alkyl, $CF_3$, $C_{3-8}$cycloalkyl, oxo or oxime.

The term "het" includes piperidinyl, morpholinyl, thiomorpholinyl, 1,1-dioxidothiomorpholinyl, piperazinyl, N—$C_{1-4}$alky substituted piperazinyl such as 4-methyl piperazinyl, pyrrolidinyl, pyridyl, imidazolyl, N—$C_{1-4}$alky substituted imidazole such as 1-methyl-1H-imidazole, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 4,5,-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl, 1-purinyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-dithiazolone. Each of these moieties may be substituted as appropriate.

The term "het" also includes azetidyl, tetrahydrofuranyl, dioxolanyl, imidazolidinyl, oxathiolanyl, oxazolidinyl.

The term "het" also includes pyran, thiopyran, tetrahydropyran or tetrahydrothiopyran.

"Amino acid," includes a residue of natural amino acid (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine, ornithine, citruline, -methyl-alanine, para-benzoylphenylalanine, phenylglycine, propargylglycine, sarcosine, and tert-butylglycine). An amino acid can conveniently be linked to the remainder of a compound of formula I through the carboxy terminus, the amino terminus, or through any other convenient point of attachment, such as, for example, through the sulfur of cysteine. In particular, an amino acid can conveniently be linked to the remainder of a compound of formula I through the carboxy terminus.

Mammal denotes human and animals. Animals specifically refers to food animal or companion animal.

It will be appreciated by those skilled in the art that compounds of the invention may have one or more chiral centers and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

Specifically, the term "$C_{1-8}$alkyl," or "$C_{1-4}$alkyl" refers to an alkyl group having one to eight or one to four carbon atoms such as, for example, methyl, ethyl, propyl, butyl, pentyl, hexyl, heptyl, octyl, and their isomeric forms thereof.

Specifically, a 5- or 6-membered heterocyclic ring includes piperidinyl, morpholinyl, thiomorpholinyl, piperazinyl, N—$C_{1-4}$alkyl substituted piperazinyl such as 4-methyl piperazinyl, or pyrrolidinyl.

Specifically, a 5- or 6-membered heterocyclic ring includes pyridyl, imidazolyl, N—$C_{1-4}$alkyl substituted imidazole such as 1-methyl-1H-imidazole.

Specifically, $R^1$ is Cl.

Specifically, $R^4$ and $R^6$ are hydrogen.

Specifically, $R^5$ is $C_{1-7}$alkyl which may be partially unsaturated and optionally substituted by OH.

Specifically, $R^5$ is $C_{1-7}$alkyl substituted by het.

Specifically, $R^5$ is $C_{1-7}$alkyl substituted by piperidinyl, morpholinyl, thiomorpholinyl, piperazinyl, pyrrolidinyl, pyridyl, imidazolyl, or tetrahydro-2H-pyran.

Specifically, $R^5$ is $C_{1-7}$alkyl substituted by morpholinyl.

Specifically, $R^5$ is $C_{1-7}$alkyl substituted by tetrahydro-2H-pyran.

Specifically, $R^5$ is $C_{1-7}$alkyl substituted by $NR^8R^9$.

Specifically, $R^8$ and $R^9$ are independently H, or $C_{1-6}$alkyl optionally substituted by one to three OH, SH, halo, phenyl, or het.

Specifically, $R^8$ and $R^9$ are independently H, or $C_{1-6}$alkyl optionally substituted by one to two OH, or phenyl.

Specifically, $R^2$ and $R^3$ are independently hydrogen, or $C_{1-7}$alkyl which may be partially unsaturated and optionally substituted by OH.

Specifically, $R^3$ is hydrogen.

Specifically, $R^3$ is halo.

Specifically, $R^2$ is hydroxymethyl.

Specifically, $R^2$ is hydroxyethyl.

Specifically, $R^2$ is $C_{1-7}$alkyl substituted by het.

Specifically, $R^2$ is $C_{1-7}$alkyl substituted by piperidinyl, morpholinyl, thiomorpholinyl, piperazinyl, pyrrolidinyl, pyridyl, imidazolyl, or tetrahydro-2H-pyran.

Specifically, $R^2$ is $C_{1-7}$alkyl substituted by 2-ethylpiperidinyl, 1,1-dioxido-4-thiomorpholinyl, 4-methylpiperazinyl.

Specifically, $R^2$ is $C_{1-7}$alkyl substituted by $NR^8R^9$.

Specifically, $R^8$ and $R^9$ are independently H, or $C_{1-6}$alkyl optionally substituted by one to three OH, SH, $CONR^{11}R^{11}$, phenyl, or het, wherein each $R^{11}$ is independently H, or $C_{1-6}$alkyl.

Specifically, $R^2$ is $C_{1-7}$alkyl substituted by $OR^{11}$ or $SR^{11}$.
Specifically, $R^{11}$ is $C_{1-4}$ alkyl or phenyl.

Specifically, a compound of the present invention is where $R^1$ is Cl; $R_2$ is hydrogen, or $C_{1-7}$alkyl which may be partially unsaturated and optionally substituted by $OR^{11}$, het, or $NR^8R^9$; $R^3$ is hydrogen or halo; $R^4$ and $R^6$ are hydrogen; and $R^5$ is $C_{1-7}$alkyl which may be partially unsaturated and optionally substituted by OH, het, or $NR^8R^9$.

Examples of the compounds of the present invention are:
(a) N (4-chlorobenzyl)-2-(hydroxymethyl)-6-oxo-6H-pyrrolo[3,2,1-ij]quinoline-5-carboxamide;
(b) N-(4-chlorobenzyl)-2-(hydroxymethyl)-6-oxo-8-(tetrahydro-2H-pyran-4-ylmethyl)-6H-pyrrolo[3,2,1-ij]quinoline-5-carboxamide;
(c) N-(4-chlorobenzyl)-2-(hydroxymethyl)-8-(4-morpholinylmethyl)-6-oxo-6H-pyrrolo[3,2,1-ij]quinoline-5-carboxamide;
(d) N-(4-chlorobenzyl)-2-(2-hydroxyethyl)-8-(4-morpholinylmethyl)-6-oxo-6H-pyrrolo[3,2,1-ij]quinoline-5-carboxamide;
(e) N-(4-chlorobenzyl)-2-(2-morpholin-4-ylethyl)-8-(4-morpholinylmethyl)-6-oxo-6H-pyrrolo[3,2,1-ij]quinoline-5-carboxamide;
(f) N-(4-chlorobenzyl)-2-[2-(diethylamino)ethyl]-8-(4-morpholinylmethyl)-6-oxo-6H-pyrrolo[3,2,1-ij]quinoline-5-carboxamide;
(g) N-(4-chlorobenzyl)-2-[2-(4-methylpiperazin-1-yl)ethyl]-8-(morpholin-4-ylmethyl)-6-oxo-6H-pyrrolo[3,2,1-ij]quinoline-5-carboxamide;
(h) N-(4-chlorobenzyl)-2-[2-(2-ethylpiperidin-1-yl)ethyl]-8-(morpholin-4-ylmethyl)-6-oxo-6H-pyrrolo[3,2,1-ij]quinoline-5-carboxamide;
(i) N-(4-chlorobenzyl)-2-[3-(4-methylpiperazin-1-yl)propyl]-8-(morpholin-4-ylmethyl)-6-oxo-6H-pyrrolo[3,2,1-ij]quinoline-5-carboxamide;
(j) N-(4-chlorobenzyl)-8-(morpholin-4-ylmethyl)-6-oxo-2-(2-piperidin-1-ylethyl)-6H-pyrrolo[3,2,1-ij]quinoline-5-carboxamide;
(k) N-(4-chlorobenzyl)-8-(morpholin-4-ylmethyl)-2-(3-morpholin-4-ylpropyl)-6-oxo-6H-pyrrolo[3,2,1-ij]quinoline-5-carboxamide;
(l) N-(4-chlorobenzyl)-2-[(1,1-dioxido-4-thiomorpholinyl)methyl]-8-(4-morpholinylmethyl)-6-oxo-6H-pyrrolo[3,2,1-ij]quinoline-5-carboxamide;
(m) N-(4-chlorobenzyl)-2-[(1,1-dioxido-4-thiomorpholinyl)methyl]-1-iodo-8-(4-morpholinylmethyl)-6-oxo-6H-pyrrolo[3,2,1-ij]quinoline-5-carboxamide;
(n) N-(4-chlorobenzyl)-2-(3-hydroxypropyl)-8-(4-morpholinylmethyl)-6-oxo-6H-pyrrolo[3,2,1-ij]quinoline-5-carboxamide;
(O) 2-{[(aminocarbonyl)amino]methyl}-N-(4-chlorobenzyl)-8-(4-morpholinylmethyl)-6-oxo-6H-pyrrolo[3,2,1-ij]quinoline-5-carboxamide;
(p) N-(4-chlorobenzyl)-2-[(1R)-1-hydroxyethyl]-8-(4-morpholinylmethyl)-6-oxo-6H-pyrrolo[3,2,1-ij]quinoline-5-carboxamide;
(q) N-(4-chlorobenzyl)-2-(methoxymethyl)-8-(4-morpholinylmethyl)-6-oxo-6H-pyrrolo[3,2,1-ij]quinoline-5-carboxamide;
(r) N-(4-chlorobenzyl)-2-[(ethylsulfanyl)methyl]-8-(4-morpholinylmethyl)-6-oxo-6H-pyrrolo[3,2,1-ij]quinoline-5-carboxamide;
(s) N-(4-chlorobenzyl)-8-(4-morpholinylmethyl)-6-oxo-2-[(phenylsulfanyl)methyl]-6H-pyrrolo[3,2,1-ij]quinoline-5-carboxamide;
(t) N-(4-chlorobenzyl)-2-[(methylamino)methyl]-8-(4-morpholinylmethyl)-6-oxo-6H-pyrrolo[3,2,1-ij]quinoline-5-carboxamide;
(u) N-(4-chlorobenzyl)-2-[(dimethylamino)methyl]-8-(4-morpholinylmethyl)-6-oxo-6H-pyrrolo[3,2,1-ij]quinoline-5-carboxamide;
(v) N-(4-chlorobenzyl)-2-(2-hydroxyethyl)-6-oxo-6H-pyrrolo[3,2,1-ij]quinoline-5-carboxamide; or
(w) N-(4-chlorobenzyl)-2-(2-hydroxyethyl)-6-oxo-8-(tetrahydro-2H-pyran-4-ylmethyl)-6H-pyrrolo[3,2,1-ij]quinoline-5-carboxamide.

Other examples of the present invention are
(a) N-(4-chlorobenzyl)-2-[2-hydroxy-1-(hydroxymethyl)ethyl]-8-(4-morpholinylmethyl)-6-oxo-6H-pyrrolo[3,2,1-ij]quinoline-5-carboxamide;
(b) N-(4-chlorobenzyl)-2-[1,2-dihydroxy-1-(hydroxymethyl)ethyl]-8-(4-morpholinylmethyl)-6-oxo-6H-pyrrolo[3,2,1-ij]quinoline-5-carboxamide;
(c) N-(4-chlorobenzyl)-2-[(ethylsulfonyl)methyl]-8-(4-morpholinylmethyl)-6-oxo-6H-pyrrolo[3,2,1-ij]quinoline-5-carboxamide;
(d) N-(4-chlorobenzyl)-2-[(ethylsulfinyl)methyl]-8-(4-morpholinylmethyl)-6-oxo-6H-pyrrolo[3,2,1-ij]quinoline-5-carboxamide;
(e) 2-{[bis(2-hydroxyethyl)amino]methyl}-N-(4-chlorobenzyl)-8-(4-morpholinylmethyl)-6-oxo-6H-pyrrolo[3,2,1-ij]quinoline-5-carboxamide;
(f) N-(4-chlorobenzyl)-2-[(2-hydroxyethoxy)methyl]-8-(4-morpholinylmethyl)-6-oxo-6H-pyrrolo[3,2,1-ij]quinoline-5-carboxamide;
(g) N-(4-chlorobenzyl)-2-(1,2-dihydroxyethyl)-8-(4-morpholinylmethyl)-6-oxo-6H-pyrrolo[3,2,1-ij]quinoline-5-carboxamide;
(h) N-(4-chlorobenzyl)-8-(4-morpholinylmethyl)-6-oxo-2-(1,2,3-trihydroxypropyl)$_6$H-pyrrolo[3,2,1-ij]quinoline-5-carboxamide;
(i) N-(4-chlorobenzyl)-2-[3-hydroxy-2-(hydroxymethyl)propyl]-8-(4-morpholinylmethyl)-6-oxo-6H-pyrrolo[3,2,1-ij]quinoline-5-carboxamide;
(j) N-(4-chlorobenzyl)-1-(hydroxymethyl)-8-(morpholin-4-ylmethyl)-6-oxo-6H-pyrrolo[3,2,1-ij]quinoline-5-carboxamide;
(k) N-(4-chlorobenzyl)-1-(2-hydroxyethyl)-8-(morpholin-4-ylmethyl)-6-oxo-6H-pyrrolo[3,2,1-ij]quinoline-5-carboxamide;
(l) N-(4-chlorobenzyl)-1-(3-hydroxypropyl)-8-(morpholin-4-ylmethyl)-6-oxo-6H-pyrrolo[3,2,1-ij]quinoline-5-carboxamide;
(m) N-(4-chlorobenzyl)-1-(2-morpholin-4-ylethyl)-8-(morpholin-4-ylmethyl)-6-oxo-6H-pyrrolo[3,2,1-ij]quinoline-5-carboxamide;
(n) N-(4-chlorobenzyl)-8-(morphol in-4-ylmethyl)-6-oxo-1-(2-thiomorpholin-4-ylethyl)-6H-pyrrolo[3,2,1-ij]quinoline-5-carboxamide;
(o) N-(4-chlorobenzyl)-1-[2-(1,1-dioxidothiomorpholin-4-yl)ethyl]-8-(morpholin-4-ylmethyl)-6-oxo-6H-pyrrolo[3,2,1-ij]quinoline-5-carboxamide;
(p) N-(4-chlorobenzyl)-1-[2-(4-methylpiperazin-1-yl)ethyl]-8-(morpholin-4-ylmethyl)-6-oxo-6H-pyrrolo[3,2,1-ij]quinoline-5-carboxamide;
(q) N-(4-chlorobenzyl)-8-(morpholin-4-ylmethyl)-6-oxo-1-(2-piperazin-1-ylethyl)-6H-pyrrolo[3,2,1-ij]quinoline-5-carboxamide;
(r) 1-[(acetylamino)methyl]-N-(4-chlorobenzyl)-8-(morpholin-4-ylmethyl)-6-oxo-6H-pyrrolo[3,2,1-ij]quinoline-5-carboxamide;
(s) N-(4-chlorobenzyl)-1-[(1S)-1-hydroxyethyl]-8-(morpholin-4-ylmethyl)-6-oxo-6H-pyrrolo[3,2,1-ij]quinoline-5-carboxamide;
(t) N-(4-chlorobenzyl)-1-(1H-imidazol-1-ylmethyl)-8-(morpholin-4-ylmethyl)-6-oxo-6H-pyrrolo[3,2,1-ij]quinoline-5-carboxamide;

(u) 1-(1H-1,2,3-benzotriazol-1-ylmethyl)-N-(4-chlorobenzyl)-8-(morpholin-4-ylmethyl)-6-oxo-6H-pyrrolo[3,2,1-ij]quinoline-5-carboxamide;

(v) N-(4-chlorobenzyl)-8-(morpholin-4-ylmethyl)-6-oxo-1-(pyridin-3-ylmethyl)-6H-pyrrolo[3,2,1-ij]quinoline-5-carboxamide;

(w) N-(4-chlorobenzyl)-8-(morpholin-4-ylmethyl)-6-oxo-1-{[({[3-(trifluoromethyl)phenyl]amino} carbonyl)amino]methyl}-6H-pyrrolo[3,2,1-ij]quinoline-5-carboxamide;

(x) N-(4-chlorobenzyl)-8-(4-morpholinylmethyl)-6-oxo-2-[2-(3-oxo-1-azetidinyl)ethyl]-6H-pyrrolo[3,2,1-ij]quinoline-5-carboxamide;

(y) N-(4-chlorobenzyl)-2-[2-(3-hydroxy-1-azetidinyl)ethyl]-8-(4-morpholinylmethyl)-6-oxo-6H-pyrrolo[3,2,1-ij]quinoline-5-carboxamide;

(z) N-(4-chlorobenzyl)-2-(2,3-dihydroxypropyl)-8-(4-morpholinylmethyl)-6-oxo-6H-pyrrolo[3,2,1-ij]quinoline-5-carboxamide;

(aa) N-(4-chlorobenzyl)-2-[(1S)-1-hydroxyethyl]-8-(4-morpholinylmethyl)-6-oxo-6H-pyrrolo[3,2,1-ij]quinoline-5-carboxamide;

(bb) N-(4-chlorobenzyl)-2-[2-(1H-imidazol-1-yl)ethyl]-8-(morpholin-4-ylmethyl)-6-oxo-6H-pyrrolo[3,2,1-ij]quinoline-5-carboxamide;

(cc) N-(4-chlorobenzyl)-2-[2-(1H-imidazol-2-yl)ethyl]-8-(morpholin-4-ylmethyl)-6-oxo-6H-pyrrolo[3,2,1-ij]quinoline-5-carboxamide;

(dd) N-(4-chlorobenzyl)-8-(morpholin-4-ylmethyl)-6-oxo-2-[2-(4H-1,2,4-triazol-3-yl)ethyl]-6H-pyrrolo[3,2,1-ij]quinoline-5-carboxamide;

(ee) N-(4-chlorobenzyl)-8-(morpholin-4-ylmethyl)-6-oxo-2-[2-(1H-tetraazol-5-yl)ethyl]-6H-pyrrolo[3,2,1-ij]quinoline-5-carboxamide;

(ff) N-(4-chlorobenzyl)-8-(morpholin-4-ylmethyl)-6-oxo-2-(2-piperazin-1-ylethyl)-6H-pyrrolo[3,2,1-ij]quinoline-5-carboxamide; or (gg) tert-butyl 4-{2-[5-{[(4-chlorobenzyl)amino]carbonyl}-8-(morpholin-4-ylmethyl)-6-oxo-6H-pyrrolo[3,2,1-ij]quinolin-2-yl]ethyl} piperazine-1-carboxylate.

The following Charts A–J describe the preparation of the compounds of formula I of the present invention. All of the starting materials are prepared by procedures described in these charts, by procedures well known to one of ordinary skill in organic chemistry or can be obtained commercially. All of the final compounds of the present invention are prepared by procedures described in these charts or by procedures analogous thereto, which would be well known to one of ordinary skill in organic chemistry. In the Charts A to J, R is $R_4$, $R_5$, or $R_6$ and i is one to three. Other variables used in the charts are as defined below or as in the claims.

As shown in Chart A, Sonogashira coupling of a 4-hydroxy-8-iodoquinoline with an acetylene employing $PdCl_2(PPh_3)_2$ and copper iodide in diethylamine solvent and subsequent cyclization under the reaction conditions provides the desired pyrroloquinolones (Blurton, et. al *Heterocycles*, 1997, 45, 2395).

CHART A

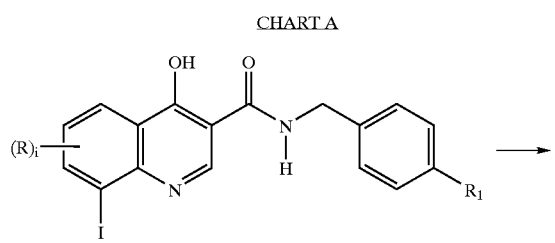

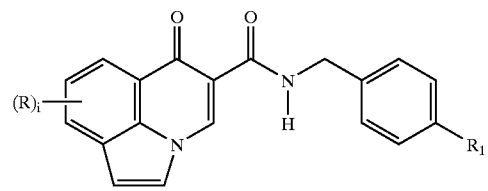

The requisite 8-iodo-4-hydroxyquinolines can be prepared according to Chart B. 2-Iodoanilines (B.2) can either be purchased from commercial sources or prepared by iodination of an aniline using reagents such as ICl. Condensation of the resulting 2-iodoaniline with diethyl ethoxymethylenemalonate and subsequent cyclization either under thermal conditions or by heating in Eaton's reagent provides the 4-hydroxy-8-iodoquinoline-3-carboxylate B.3. Amide formation can be accomplished by treatment with a neat amine (e.g. 4-chlorobenzylamine) at elevated temperatures to provide the 4-hydroxy-8-iodoquinoline-3-carboxamide B.4.

CHART B

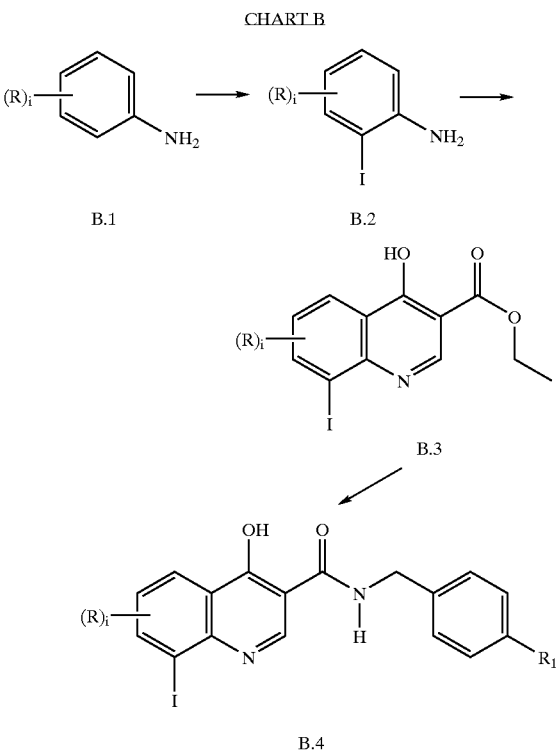

Some of the substituted anilines can be prepared according to Chart C and Chart D. For carbon-substituted anilines, Wittig reaction between (4-nitrobenzyl)(triphenyl)phosphonium bromide (C.2) and the desired aldehyde provides the nitrobenzylidine C.3. Hydrogenation over $PtO_2$ reduces the nitro group and the olefin to provide the corresponding aniline C.4. Iodination and quinoline formation as described in Chart B then provides the desired 8-iodo-4-hydroxyquinoline C.7.

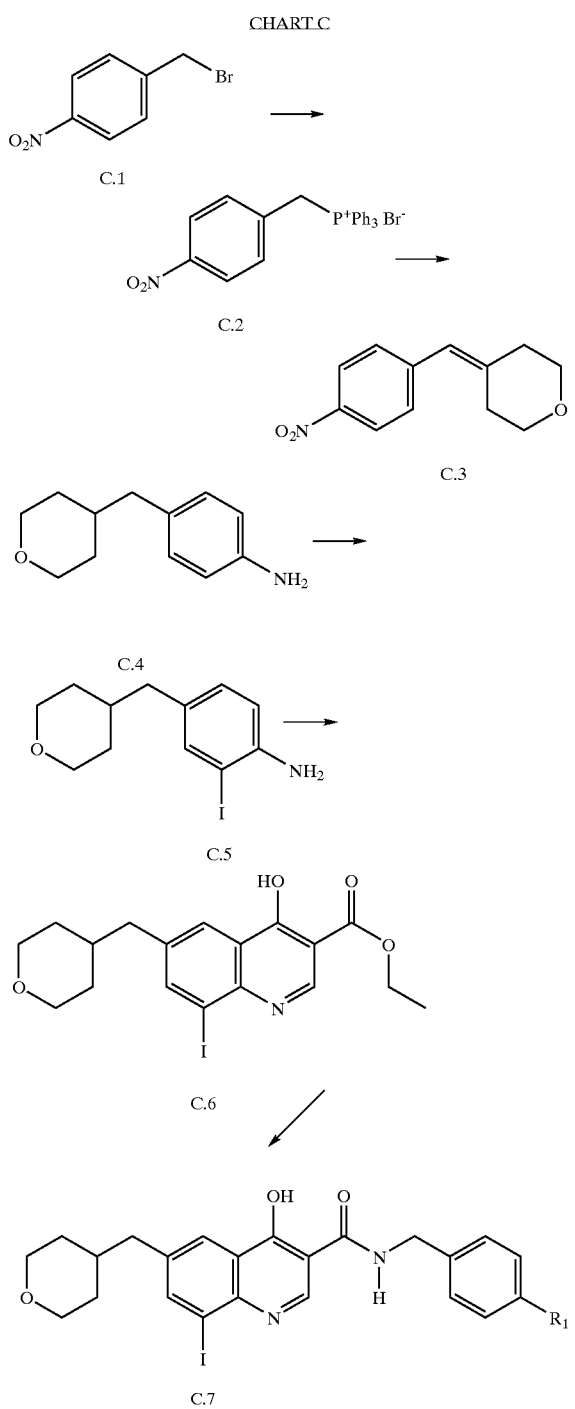

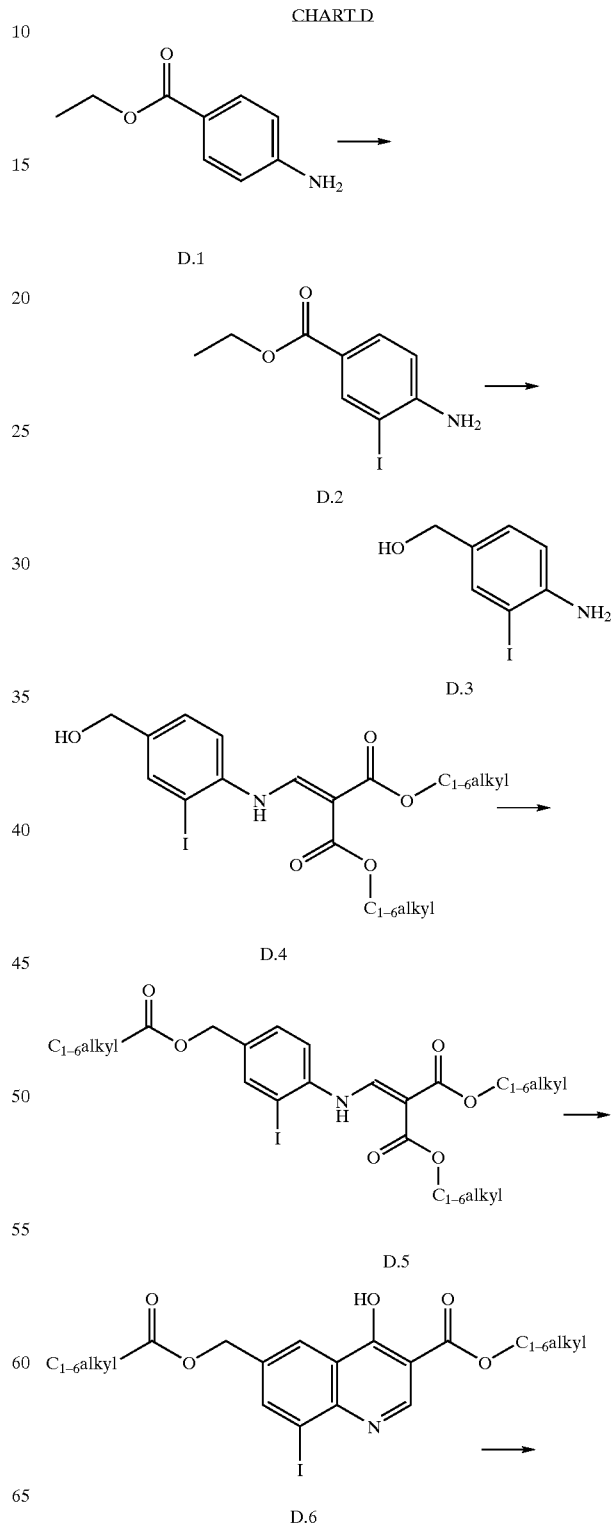

elevated temperatures results in amide formation and deprotection of the alcohol to give the hydroxymethyl quinoline D.7. At this point, the hydroxyl group can be alkylated or mesylated with methanesulfonyl chloride and displaced with a nucleophile (e.g. morpholine) to give the desired 8-iodoquinoline D.8.

Aminomethyl, hydroxymethyl, alkoxymethyl, etc. substituted analogs can be prepared as shown in Chart D. Iodination of 4-aminobenzoate using NIS provides the 2-iodoaniline D.2. Reduction of the ester with DIBAL-H provides the hydroxymethyliodoaniline D.3. Condensation of the aniline with neat diethyl ethoxymethylenemalonate at elevated temperatures provides the enamine D.4. Protection of the alcohol with acetic anhydride in acetic acid solvent gives D.5. Cyclization in refluxing diphenylether provides the 8-iodo-4-hydroxyquinoline-3-carboxylate D.6. Treatment with a neat amine (e.g. 4-chlorobenzylamine) at

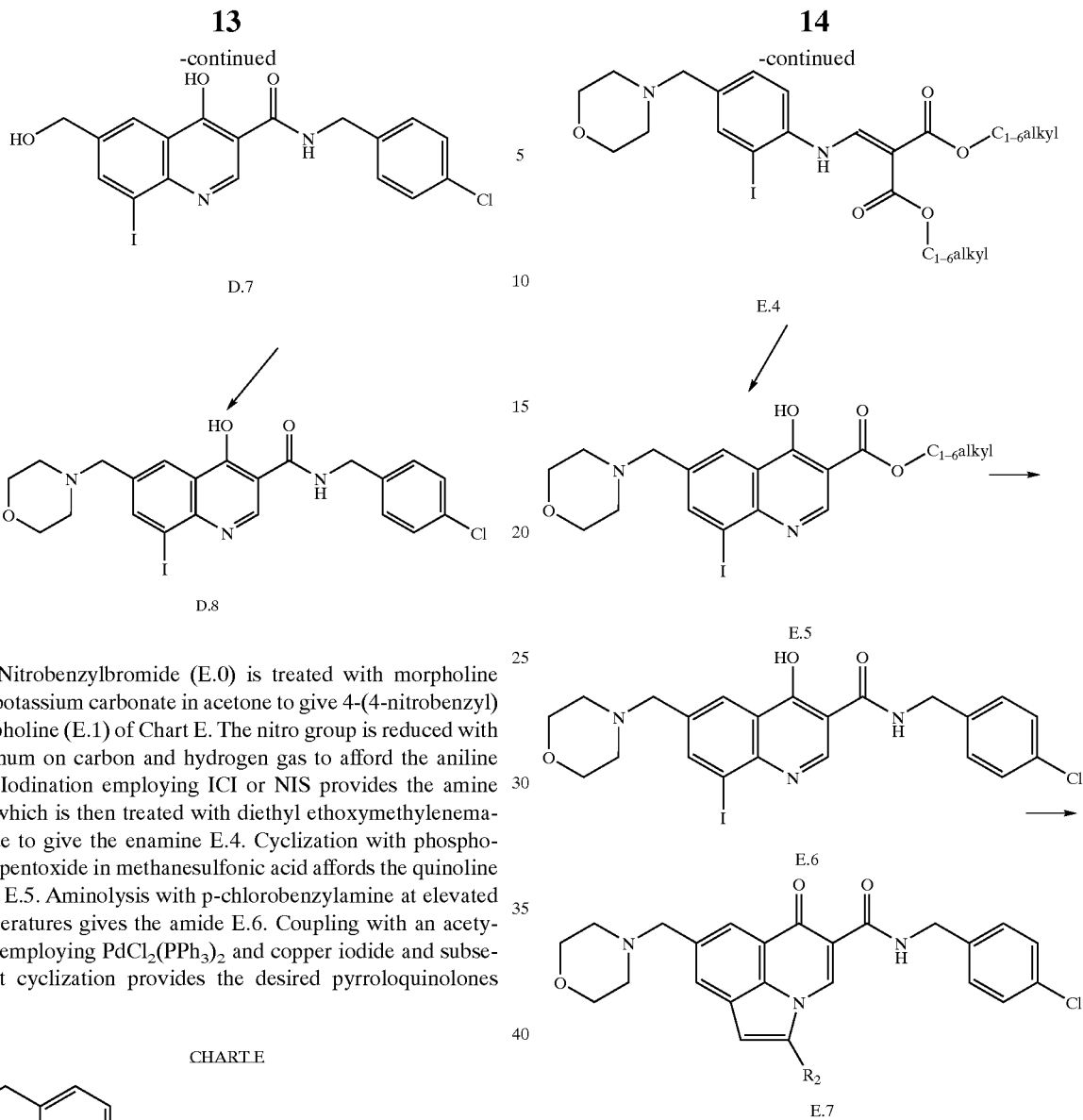

4-Nitrobenzylbromide (E.0) is treated with morpholine and potassium carbonate in acetone to give 4-(4-nitrobenzyl) morpholine (E.1) of Chart E. The nitro group is reduced with platinum on carbon and hydrogen gas to afford the aniline E.2. Iodination employing ICI or NIS provides the amine E.3 which is then treated with diethyl ethoxymethylenemalonate to give the enamine E.4. Cyclization with phosphorous pentoxide in methanesulfonic acid affords the quinoline ester E.5. Aminolysis with p-chlorobenzylamine at elevated temperatures gives the amide E.6. Coupling with an acetylene employing $PdCl_2(PPh_3)_2$ and copper iodide and subsequent cyclization provides the desired pyrroloquinolones E.7.

As shown in Chart F, palladium catalyzed heteroannulation of internal alkynes using appropriately substituted 2-iodoanilines F.0 provides the indoles F.1 (Larock et al. *J. Am. Chem. Soc.,* 1991, 113, 6689). Reduction of the corresponding indoles provides the indolines F.2. Condensation of the indoline F.2 with diethyl ethoxymethylenemalonate affords enamine F.3. Cyclization using Eaton's reagent provides ester F.4. Amide formation using neat amine gives amide F.5. Oxidation provides the corresponding indoles F.6.

CHART F

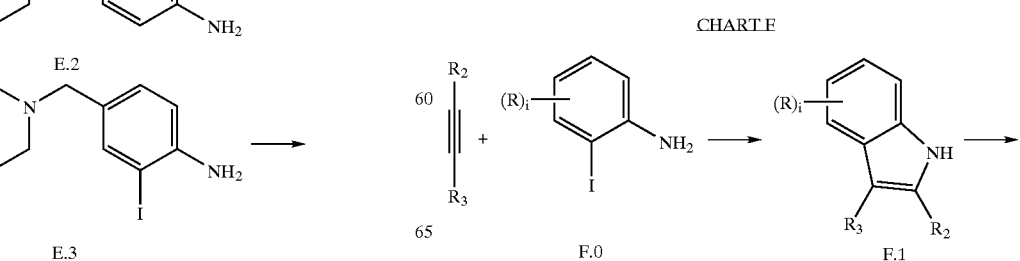

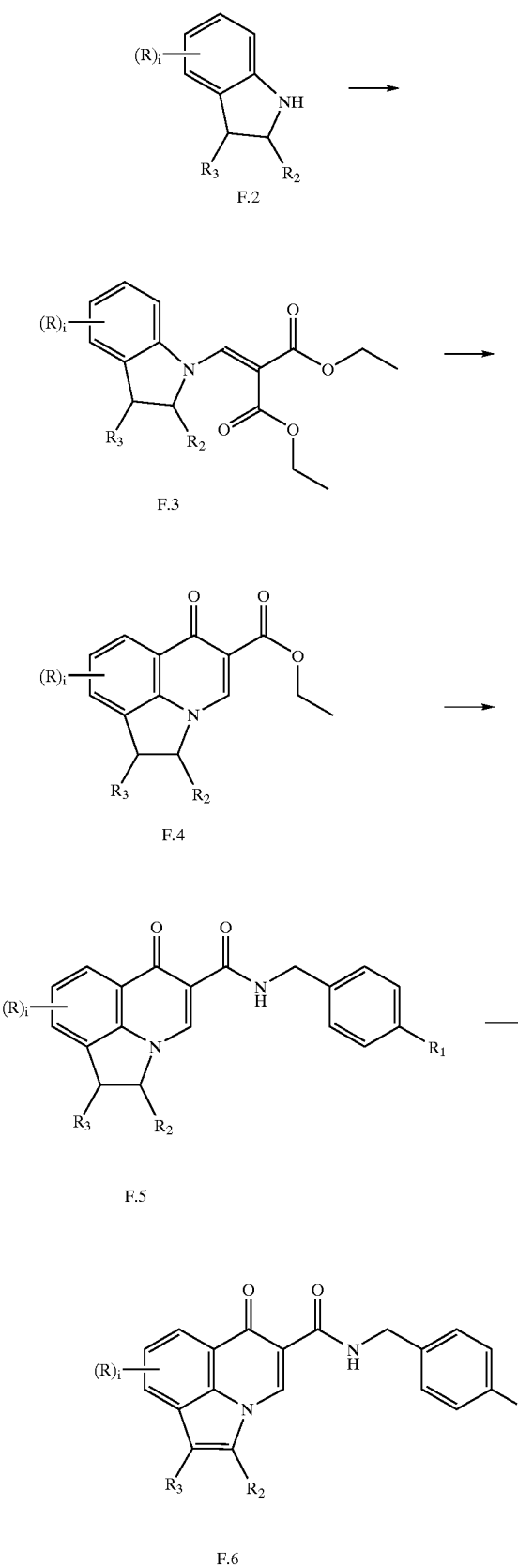

F.2

F.3

F.4

F.5

F.6

In Chart G alkylation of amide B.4 (preparation described in Chart B) with a suitably substituted propargyl bromide provides the N-propargyl-8-iodoquinoline-3-carboxamide G.1. Palladium catalyzed tandem cyclization-hydride ion capture (Grigg et al. *Tetrahedron Lett.*, 1988, 34, 4325) provides the alkylidene indolines G.2. Isomerization of the exocylic G.2 double bond provides indoles G.3.

CHART G

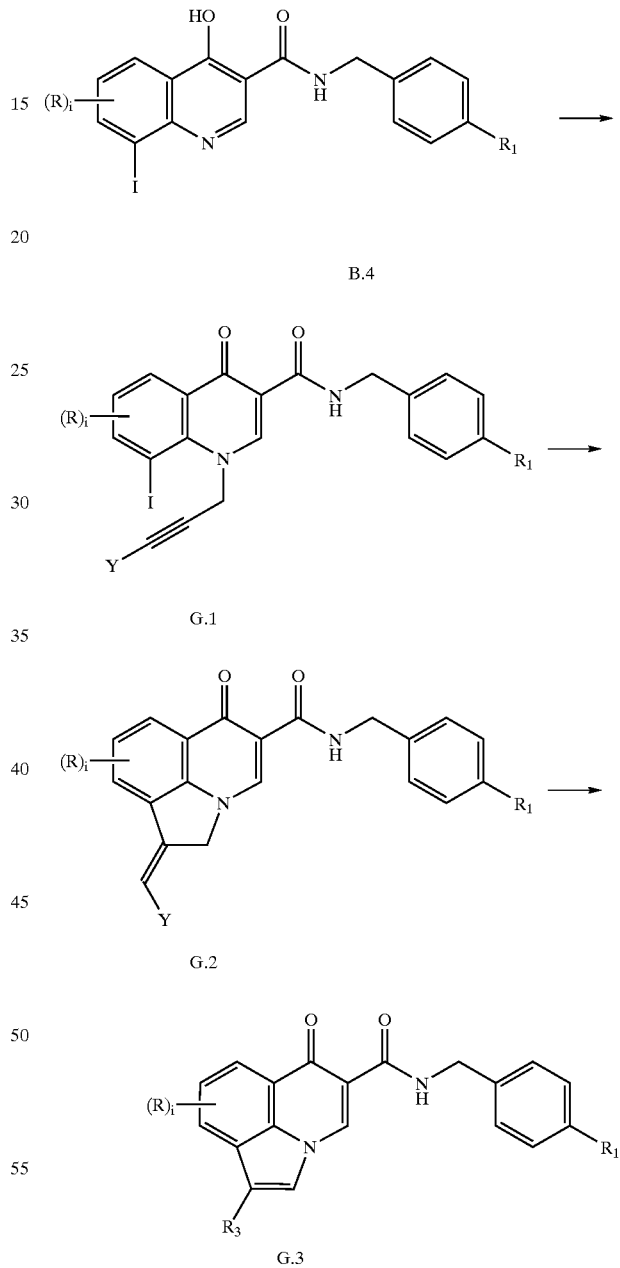

B.4

G.1

G.2

G.3

A synthesis of compounds, where $R_2$ and $R_3$ of formula I are not hydrogen, is shown in Chart H (where X=Br or I). Compound H.1, synthesis given in Chart A, is iodinated or brominated to produce H.2. Application of the appropriate coupling protocol provides H.3. Nonexclusive examples of the appropriate couplings are the Suzuki, Stille and Negishi reactions.

CHART H

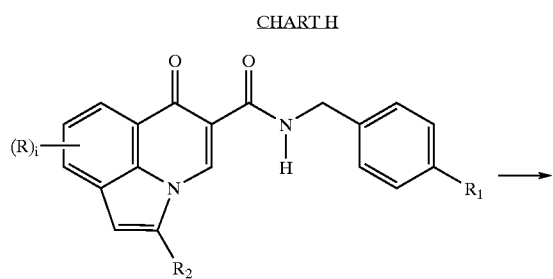

H.1

H.2

H.3

Chart I (where alkyl =$C_{1-7}$ and Q=$OC_{1-7}$ alkyl or $C_{1-7}$ alkyl) describes the preparation of compounds 1.4. Alkoxycarbonylation of 1.0, previously described in Chart B, using a palladium catalyst contacted with CO in the presence of the appropriate alcohol provides ester 1.1. Nitrogen alkylation of 1.1 is accomplished by contacting with $Cs_2CO_3$ or $K_2CO_3$ or another suitable base in the presence of a bromo-, iodo- or chloromethyl ketone or 2-bromo, 2-iodo- or 2-chloroacetate to provide 1.2. 1.2 is converted to 1.3, or its keto variant, by Dieckmann cyclization in the presence of the appropriate base, for example KOt-Bu. Triflation of the hydroxy moiety in 1.3 followed by palladium, or another appropriate metal, catalyzed coupling yields 1.4. Alternatively, treatment of compounds occupying predominantly the keto form of 1.3 with a reactive nucleophile, for example a Grignard reagent, followed by acid catalyzed elimination also provides 1.4.

CHART I

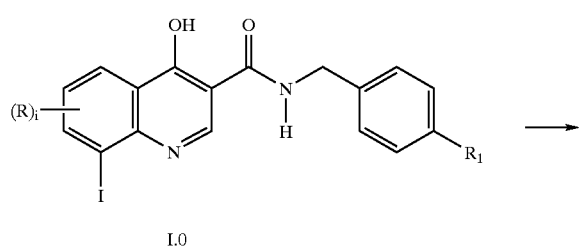

I.0

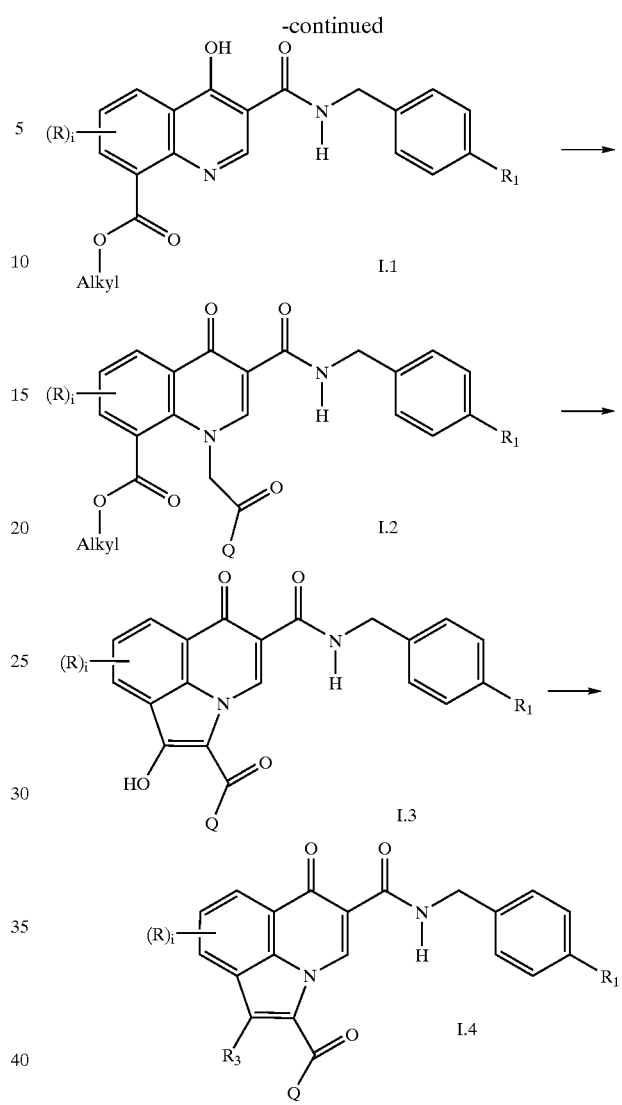

I.1

I.2

I.3

I.4

For Chart J (where B=$OC_{1-7}$ alkyl or $C_{1-7}$ alkyl, and Z and L are subsets of $R_2$ and $R_3$), J.1 is prepared as described in Chart A with the appropriate propargyl alcohol. J.1 is converted into J.2 by first transient formation of an L and B substituted enol ether or ester enolate equivalent and subsequent rearrangement. A nonexclusive example of the [3.3]-sigmatropic rearrangement is the Claisen rearrangement. Selected J.2 compounds spontaneously convert to J.3 or are isomerized with acid catalysis.

CHART J

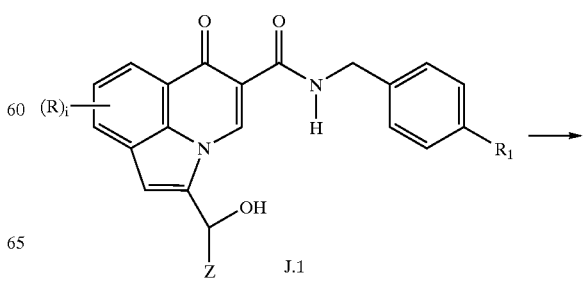

J.1

-continued

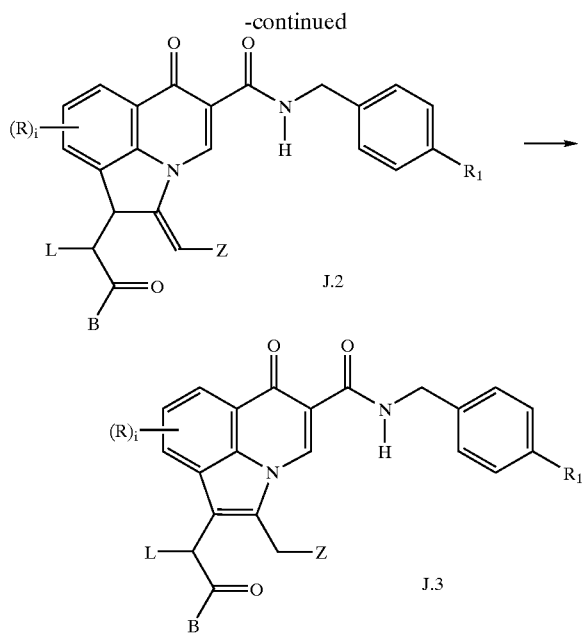

It will be apparent to those skilled in the art that the described synthetic procedures are merely representative in nature and alternative synthetic processes are known to one of ordinary skill in organic chemistry.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, etoglutarate, and glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

"Pharmaceutically acceptable salts" refers to those salts which possess the biological effectiveness and properties of the parent compound and which are not biologically or otherwise undesirable.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975).

The compounds and compositions of the present invention can be administered parenterally (for example, by intravenous, intraperitoneal or intramuscular injection), topically, orally, intravaginally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The exact regimen for administration of the compounds and compositions disclosed herein will necessarily be dependent upon the needs of the individual subject being treated, the type of treatment and, of course, the judgment of the attending practitioner.

The antiviral activity of a compound of the invention can be determined using pharmacological models which are well known to the art, or using Test A described below.

The compounds of formula (I) and pharmaceutically acceptable salts thereof are useful as antiviral agents. Thus, they are useful to combat viral infections in animals, including man. The compounds are generally active against herpesviruses, and are particularly useful against the varicella zoster virus, the Epstein-Barr virus, the herpes simplex virus, the human herpesvirus type 8 (HHV-8) and the cytomegalovirus (CMV).

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 $\mu$l volume with 5.4 mM HEPES (pH 7.5), 11.7 mM KCl, 4.5 mM $MgCl_2$, 0.36 mg/ml BSA, and 90 nM $^3$H-dTTP. Assays are run with and without CHAPS, (3-[(3-Cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 $\mu$g/ml BSA, and 0.01% sodium azide. The HCMV polymerase, which is expressed in recombinant baculovirus-infected SF-9 cells and purified according to literature procedures, is added at 10% (or 10 $\mu$l) of the final reaction volume, i.e., 100 $\mu$l. Compounds are diluted in 50% DMSO and 10 $\mu$l are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25° C. or 37° C. $H_2O$ bath and terminated via the addition of 40 $\mu$l/reaction of 0.5 M EDTA (pH 8) per well. Reactions are terminated within the timeframe during which substrate incorporation is linear and varied depending upon the enzyme and conditions used, i.e., 30 min. for HCMV polymerase. Ten $\mu$l of streptavidin-SPA beads (20 mg/ml in PBS/10% glycerol) are added following termination of the reaction. Plates are incubated 10 min. at 37° C., then equilibrated to room temperature, and counted on a Packard Topcount. Linear regressions are performed and $IC_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Results of the testing of representative compounds of formula I in this assay are shown in Table 1 below.

TABLE 1

Biological Data

| Examples | CMV Polymerase IC$_{50}$ ($\mu$M) | HSV Polymerase IC$_{50}$ ($\mu$M) | VZV Polymerase IC$_{50}$ ($\mu$M) |
|---|---|---|---|
| 1 | 1.2 | n.d. | n.d. |
| 2 | 0.21 | 0.20 | 0.16 |
| 3 | 0.53 | 0.51 | 0.25 |
| 4 | 0.35 | 0.12 | 0.20 |
| 5 | 0.48 | n.d. | n.d. |
| 6 | 2.43 | n.d. | n.d. |
| 7 | 1.76 | n.d. | n.d. |
| 8 | 1.92 | n.d. | n.d. |
| 9 | 3.44 | n.d. | n.d. |
| 10 | 2.30 | n.d. | n.d. |
| 11 | 3.57 | n.d. | n.d. |
| 12 | 0.36 | n.d. | n.d. |
| 13 | 0.84 | n.d. | n.d. |
| 14 | 0.32 | n.d. | n.d. |
| 15 | 0.41 | n.d. | n.d. |
| 16 | 0.26 | n.d. | n.d. |
| 17 | 0.54 | n.d. | n.d. |
| 18 | 0.58 | n.d. | n.d. |
| 19 | 0.68 | n.d. | n.d. |
| 20 | 0.49 | n.d. | n.d. |
| 21 | 0.62 | n.d. | n.d. |
| 22 | 1.2 | n.d. | n.d. |
| 23 | 0.13 | 0.14 | 0.1 |

At the table, the term "n.d." refers to "not determined".

The compounds and their preparation of the present invention will be better understood in connection with the following examples, which are intended as an illustration of and not a limitation upon the scope of the invention.

EXAMPLES

Example 1

N-(4-Chlorobenzyl)-2-(hydroxymethyl)-6-oxo-6H-pyrrolo[3,2,1-ij]quinoline-5-carboxamide

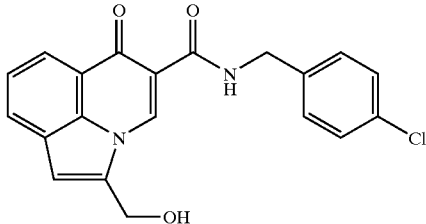

A solution of N-(4-chlorobenzyl)-4-hydroxy-8-iodo-3-quinolinecarboxamide (prepared according to the general procedure in WO 9932450, 0.53 g), copper iodide (0.11 g), bis(triphenylphosphine)palladium(II) chloride (0.043 g) and propargyl alcohol (0.085 mL) in 20 mL diethylamine is stirred at room temperature for 18 h. The solid in the reaction mixture is filtered, washed with hexanes and dried. The solid is dissolved in CH$_2$Cl$_2$/MeOH and adsorbed onto silica. Purification by chromatography (gradient from CH$_2$Cl$_2$ to 3% MeOH/CH$_2$Cl$_2$) affords N-(4-chlorobenzyl)-2-(hydroxymethyl)-6-oxo-6H-pyrrolo[3,2,1-ij]quinoline-5-carboxamide as a white solid (0.23 g, 52%), m.p. 211–213° C.

$^1$H NMR (300 MHz, DMSO-d$_6$) δ 10.13, 9.30, 8.09, 8.07, 7.65, 7.38, 7.05, 5.79, 4.90, 4.57; IR 3345, 1663, 1631, 1593, 1549, 1488, 1468, 1323, 1302, 1269, 1225, 1032, 814, 800, 758 cm$^{-1}$.

Preparation 1 (4-Nitrobenzyl)(triphenyl)phosphonium bromide

To a solution of triphenylphosphine (25.92 g) in 300 mL CH$_2$Cl$_2$ is added 4-nitrobenzylbromide (31.47 g). The solution is allowed to stir overnight. The mixture is concentrated. The resulting solid is triturated with Et$_2$O, filtered and dried to yield 54.58 g (95%) of (4-nitrobenzyl)(triphenyl)phosphonium bromide as a white solid.

$^1$H NMR (300 MHz, CDCl$_3$) δ 7.81, 7.75, 7.61, 7.47, 5.99.

Preparation 2 4-(4-Nitrobenzylidene)tetrahydro-2H-pyran

To a 500 mL 3-necked flask is added NaH (2.0 g of a 60% suspension in mineral oil) and 35 mL of DMSO. The resulting solution is heated at 80° C. for 1 h then cooled in an ice-water bath. To this is then added a solution of the (4-nitrobenzyl)(triphenyl)phosphonium bromide (23.92 g) in 200 mL warm DMSO. The mixture is stirred at room temperature for 1 h. Tetrahydro-4H-pyran-4-one (4.62 mL) is then added. The mixture is allowed to stir overnight at room temperature and then at 80° C. for 2 days. The mixture is poured over ice and extracted with Et$_2$O. The combined organic extracts are dried and condensed. Chromatography (Biotage flash 40S, gradient from hexanes to 80% CH$_2$Cl$_2$/hexanes) yields 4.83 g (44%) of 4-(4-nitrobenzylidene)tetrahydro-2H-pyran as a solid.

$^1$H NMR (300 MHz, CDCl$_3$) δ 8.19, 7.35, 6.38, 3.82, 3.70, 2.55, 2.46.

Preparation 3 2-Iodo-4-(tetrahydro-2H-pyran-4-ylmethyl)aniline

A mixture of 4-(4-nitrobenzylidene)tetrahydro-2H-pyran (2.0 g) and PtO$_2$ (0.2 g) is hydrogenated at 40 p.s.i. H$_2$ for 3.5 h. The mixture is filtered through celite and the filtrate is condensed. The crude residue is dissolved in a mixture of 40 mL CHCl$_3$ and 4 mL MeOH. To this is added sodium acetate (2.24 g), followed by the dropwise addition of a solution of ICl (0.69 mL) in MeOH (10 mL). The reaction is stirred at room temperature for 1 h then quenched by pouring into an iced saturated solution of aqueous sodium bisulfite (200 mL). The mixture is stirred for 30 minutes then concentrated to remove organic solvents. The aqueous solution is extracted with CH$_2$Cl$_2$ (3×). The combined organic layers are washed with brine, dried and condensed. The crude product is chromatographed (Biotage flash 40M, eluant CH$_2$Cl$_2$) to yield 1.0 g (34%) of 2-iodo-4-(tetrahydro-2H-pyran-4-ylmethyl)aniline as an oil.

$^1$H NMR (300 MHz, CDCl$_3$) δ 7.47, 6.95, 6.76, 3.95, 3.34, 2.41, 1.68, 1.56, 1.31; OAMS supporting ions at: ESI+ 318.1.

Preparation 4 Ethyl 4-hydroxy-8-iodo-6-(tetrahydro-2H-pyran-4-ylmethyl)-3-quinolinecarboxylate A mixture of 2-iodo-4-(tetrahydro-2H-pyran-4-ylmethyl)aniline (1.0 g) and diethyl ethoxymethylenemalonate (0.70 mL) is heated to 130° C. for 1 h. The mixture is cooled to room temperature. Diphenyl ether (20 mL) is added and the reaction is heated to 250° C. for 1 h. The mixture is cooled and the resulting solid is collected and washed with hexanes. The crude product is chromatographed (Biotage flash 40M, eluant 2% MeOH/CH$_2$Cl$_2$) to yield 0.80 g (58%) of ethyl 4-hydroxy-8-iodo-6-(tetrahydro-2H-pyran-4-ylmethyl)-3-quinolinecarboxylate as a solid, m.p. 218–222° C. (dec).

$^1$H NMR (300 MHz, DMSO-d$_6$) δ 11.18, 8.45, 8.09, 7.95, 4.22, 3.80, 3.22, 2.61, 1.76, 1.45, 1.27, 1.20; IR (drift) 3073, 2928, 2918, 1709, 1619, 1600, 1560, 1517, 1327, 1292, 1216, 1170, 1154, 1135, 1090 cm$^{-1}$; HRMS (FAB) calcd for C$_{18}$H$_{20}$NO$_4$+H$_1$ 442.0517, found 442.0526; Anal. calcd for C$_{18}$H$_{20}$NO$_4$: C, 48.99; H, 4.57; N, 3.17, found: C, 49.09; H, 4.58; N, 3.24.

Preparation 5 N-(4-Chlorobenzyl)-4-hydroxy-8-iodo-6-(tetrahydro-2H-pyran-4-ylmethyl)-3-quinolinecarboxamide A suspension of ethyl 4-hydroxy-8-iodo-6-(tetrahydro-2H-pyran-4-ylmethyl)-3-quinolinecarboxylate (0.8 g) and 4-chlorobenzylamine (1.54 mL) is heated to 180° C. for 1 h. The reaction is cooled to room temperature. The resulting solid is collected and washed with Et$_2$O. The crude solid is adsorbed onto silica and chromatographed (Biotage flash 40S, eluant 1% MeOH/CH$_2$Cl$_2$ then 2% MeOH/CH$_2$Cl$_2$). Fractions homogeneous by TLC are combined and concentrated. The resulting solid is triturated with EtOAc/hexanes to yield 0.73 g (75%) of N-(4-chlorobenzyl)-4-hydroxy-8-iodo-6-(tetrahydro-2H-pyran-4-ylmethyl)-3-quinolinecarboxamide as a white solid, m.p. 257–259° C.

$^1$H NMR δ 10.39, 8.70, 8.15, 8.04, 7.38, 4.54, 3.80, 3.22, 2.63, 1.79, 1.48, 1.24; IR (drift) 2925, 1654, 1596, 1554, 1513, 1493, 1099, 1090, 850, 828, 811, 799, 781, 766, 724 cm$^{-1}$; OAMS supporting ions at: ESI+ 536.7, ESI– 534.7; Anal. calcd for C$_{23}$H$_{22}$ClIN$_2$O$_3$: C, 51.46; H, 4.13; N, 5.22, found: C, 51.31; H, 4.13; N, 5.20.

Example 2

N-(4-Chlorobenzyl)-2-(hydroxymethyl)-6-oxo-8-(tetrahydro-2H-pyran-4-ylmethyl)-6H-pyrrolo[3,2,1-ij]quinoline-5-carboxamide

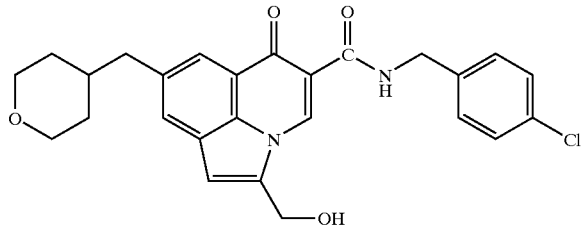

To a solution of N-(4-chlorobenzyl)-4-hydroxy-8-iodo-6-(tetrahydro-2H-pyran-4-ylmethyl)-3-quinolinecarboxamide (0.185 g), PdCl$_2$(PPh$_3$)$_2$ (0.012 g), and CuI (0.032 g) in 10 mL of diethylamine is added propargyl alcohol (0.02 mL). The reaction is stirred overnight. The mixture is concentrated and the resulting solid is partitioned between CH$_2$Cl$_2$ and water. The aqueous layer is extracted with CH$_2$Cl$_2$ (3×). The combined organic layers are washed with brine, dried and condensed. The crude product is chromatographed (Biotage flash 40S, gradient from CH$_2$Cl$_2$ to 2% MeOH/CH$_2$Cl$_2$). Fractions homogeneous by TLC are combined and concentrated. The resulting solid is recrystallized from CH$_2$Cl$_2$/Et$_2$O to yield 0.09 g (56%) of N-(4-chlorobenzyl)-2-(hydroxymethyl)-6-oxo-8-(tetrahydro-2H-pyran-4-ylmethyl)-6H-pyrrolo[3,2,1-ij]quinoline-5-carboxamide as a white solid, m.p. 196–198° C.

$^1$H NMR (300 MHz, DMSO-d$_6$) δ 10.20, 9.30, 7.94, 7.88, 7.40, 7.02, 5.78, 4.90, 4.59, 3.80, 3.22, 2.79, 1.83, 1.48, 1.26; IR (drift) 3357, 2925, 1663, 1633, 1586, 1568, 1543, 1492, 1311, 1242, 1233, 1086, 852, 808, 799 cm$^{-1}$; MS (EI) m/z 464 (M$^+$), 464, 297, 154, 140, 140, 89, 77, 55, 51, 51; Anal. calcd for C$_{26}$H$_{25}$ClN$_2$O$_4$: C, 67.17; H, 5.42; N, 6.03; found: C, 66.91; H, 5.48; N, 6.03.

Preparation 6 Ethyl 4-amino-3-iodobenzoate

To a solution of ethyl 4-aminobenzoate (13.0 g) in DMF (33 mL) is added a solution of N-iodosuccinimide (18.6 g) in DMF (39 mL). The reaction is stirred at room temperature overnight. The mixture is poured into 800 mL water. The resulting solid is collected and dried to yield 20.7 g (90%) of the titled compound, m.p. 71–74° C.

$^1$H NMR (300 MHz, DMSO-d$_6$) δ 8.10, 7.65, 6.74, 4.21, 1.27; IR (drift) 3455, 3364, 1688, 1615, 1592, 1364, 1324, 1292, 1286, 1249, 1152, 1127, 818, 762, 671 cm$^{-1}$; OAMS supporting ions at: ESI+ 291.9, ESI– 289.9; Anal. calcd for C$_9$H$_{10}$INO$_2$: C, 37.14; H, 3.46; N, 4.81, found: C, 37.02; H, 3.44; N, 4.81.

Preparation 7 (4-Amino-3-iodophenyl)methanol

To a solution of ethyl 4-amino-3-iodobenzoate (8.0 g) in CH$_2$Cl$_2$ (56 mL) cooled to 0° C. is added diisobutylaluminum hydride in CH$_2$Cl$_2$ (110 mL of a 1M solution). The reaction is stirred at 0° C. for 2 h then quenched by the addition of MeOH (50 mL). To this is added 1N HCl (100 mL). The mixture is concentrated to remove the organics. The aqueous solution is extracted with CH$_2$Cl$_2$ (3×). The combined organic layers are dried over Na$_2$SO$_4$, filtered and condensed. The resulting residue is adsorbed onto silica and chromatographed (Biotage flash 40M, gradient from CH$_2$Cl$_2$ to 2% MeOH/CH$_2$Cl$_2$). Fractions homogeneous by TLC are combined and condensed to afford (4-amino-3-iodophenyl)methanol.

$^1$H NMR (300 MHz, DMSO-d$_6$) δ 7.49, 7.01, 6.70, 6.00, 4.95, 4.28.

Preparation 8 Diethyl 2-{[4-(hydroxymethyl)-2-iodoanilino]methylene}malonate

A solution of (4-amino-3-iodophenyl)methanol (5.97 g) and diethyl ethoxymethylenemalonate (5.34 mL) is heated at 100° C. for 30 min. The reaction is cooled to room temperature. The resulting solid is dissolved in a mixture of CH$_2$Cl$_2$ and MeOH, adsorbed onto silica and chromatographed (Biotage flash 40M, eluant CH$_2$Cl$_2$, then 0.5% MeOH/CH$_2$Cl$_2$). Product containing fractions are combined and condensed to afford diethyl 2-{[4-(hydroxymethyl)-2-iodoanilino]methylene}malonate as a white solid, m.p. 152–154° C.

$^1$H NMR (300 MHz, DMSO-d$_6$) δ 11.0, 8.43, 7.83, 7.47, 7.38, 5.29, 4.45, 4.23, 4.14, 1.27, 1.25; IR (drift) 1680, 1644, 1593, 1423, 1384, 1373, 1349, 1296, 1285, 1267, 1242, 1202, 1036, 1004, 798 cm$^{-1}$; OAMS supporting ions at: ESI+ 419.7, ESI– 417.8; Anal. calcd for C$_{15}$H$_{18}$INO$_5$: C, 42.98; H, 4.33; N, 3.34, found: C, 42.73; H, 4.21; N, 3.33.

Preparation 9 Diethyl 2-({4-[(acetyloxy)methyl]-2-iodoanilino}methylene) malonate A solution of diethyl 2-{[4-(hydroxymethyl)-2-iodoanilino]methylene}malonate (0.20 g) and acetic anhydride (0.054 mL) in acetic acid (0.24 mL) is heated at 80° C. overnight. The reaction is cooled to room temperature and poured into 50 mL of water. The resulting solid is filtered and dried to yield 0.19 g (87%) of diethyl 2-({4-[(acetyloxy)methyl]-2-iodoanilino} methylene)malonate as a white solid, m.p. 128–131° C.

$^1$H NMR (300 MHz, DMSO-d$_6$) δ 10.99, 8.44, 7.91, 7.51, 7.44, 5.01, 4.24, 4.14, 2.06, 1.27, 1.25; IR (drift) 1737, 1686, 1648, 1600, 1428, 1362, 1349, 1299, 1267, 1248, 1209, 1039, 1023, 809, 797 cm$^{-1}$; OAMS supporting ions at: ESI+ 461.7, ESI– 459.7; Anal. calcd for C$_{17}$H$_{20}$INO$_6$: C, 44.27; H, 4.37; N, 3.04, found: C, 44.39; H, 4.37; N, 3.09.

Preparation 10 Ethyl 6-[(acetyloxy)methyl]-4-hydroxy-8-iodo-3-quinolinecarboxylate A solution of diethyl 2-({4-[(acetyloxy)methyl]-2-iodoanilino}methylene)malonate (1.75 g) in Ph$_2$O (20 mL)

is heated at 250° C. for 40 min. The reaction is cooled to room temperature and diluted with hexanes. The resulting solid is collected and dried. The crude solid is adsorbed onto silica and chromatographed (Biotage flash 40S, gradient from $CH_2Cl_2$ to 2% $MeOH/CH_2Cl_2$). Product containing fractions are combined and concentrated to yield 0.98 g (62%) of ethyl 6-[(acetyloxy)methyl]-4-hydroxy-8-iodo-3-quinolinecarboxylate, m.p. 119–123° C.

$^1$H NMR (300 MHz, DMSO-$d_6$) δ 11.29, 8.48, 8.23, 8.16, 5.15, 4.23, 2.09, 1.28; IR (drift) 2993, 2956, 1738, 1711, 1602, 1550, 1524, 1331, 1293, 1284, 1242, 1218, 1172, 1093, 1035 cm$^{-1}$; HRMS (FAB) calcd for $C_{15}H_{14}INO_5+H_1$ 415.9997, found 416.0000; Anal. calcd for $C_{15}H_{14}INO_5$: C, 43.39; H, 3.40; N, 3.37, found: C, 43.55; H, 3.39; N, 3.73.

Preparation 11 N-(4-Chlorobenzyl)-4-hydroxy-6-(hydroxymethyl)-8-iodo-3-quinolinecarboxamide A suspension of ethyl 6-[(acetyloxy)methyl]-4-hydroxy-8-iodo-3-quinolinecarboxylate (0.90 g) and 4-chlorobenzylamine (2.6 mL) is heated at 180° C. for 1 h. The reaction is cooled to room temperature and diluted with $Et_2O$. The resulting solid is filtered and triturated with acetone to yield 0.74 g (73%) of N-(4-chlorobenzyl)-4-hydroxy-6-(hydroxymethyl)-8-iodo-3-quinolinecarboxamide, m.p. 283–286° C.

$^1$H NMR (300 MHz, DMSO-$d_6$) δ 11.61, 10.29, 8.71, 8.23, 7.38, 5.46, 4.60, 4.55; IR (drift) 3369, 3235, 1654, 1598, 1556, 1517, 1491, 1351, 1281, 1213, 1181, 1069, 811, 799, 723 cm$^{-1}$; OAMS supporting ions at: ESI+ 468.6, ESI- 466.6; Anal. calcd for $C_{18}H_{14}ClIN_2O_3$: C, 46.13; H, 3.01; N, 5.98, found: C, 46.12; H, 2.99; N, 5.99.

Preparation 12 N-(4-Chlorobenzyl)-4-hydroxy-8-iodo-6-(4-morpholinylmethyl)-3-quinolinecarboxamide To a solution of N-(4-chlorobenzyl)-4-hydroxy-6-(hydroxymethyl)-8-iodo-3-quinolinecarboxamide (0.36 g), DMAP (0.016 g) and collidine (0.12 mL) in 13 mL DMF at 0° C. is added methanesulfonyl chloride (0.065 mL). The solution is allowed to warm to room temperature and is stirred overnight. Morpholine (0.67 mL) is then added and the solution is stirred at room temperature overnight. The mixture is poured into water. The resulting solid is collected and dried. The crude product is adsorbed onto silica and chromatographed (Biotage flash 40S, eluant 1% $MeOH/CH_2Cl_2$, then 2% $MeOH/CH_2Cl_2$). Product containing fractions are combined and concentrated to yield 0.322 g (78%) of N-(4-chlorobenzyl)-4-hydroxy-8-iodo-6-(4-morpholinylmethyl)-3-quinolinecarboxamide, m.p. 230–233° C.

$^1$H NMR (300 MHz, DMSO-$d_6$) δ 11.63, 10.28, 8.71, 8.23, 8.19, 7.38, 4.55, 3.57, 2.37; OAMS supporting ions at: ESI+ 537.8, ESI- 535.8; Anal. calcd for $C_{22}H_{21}ClIN_3O_3$: C, 49.13; H, 3.94; N, 7.81; Cl, 6.59, found: C, 49.38; H, 4.07; N, 7.65.

Example 3

N-(4-Chlorobenzyl)-2-(hydroxymethyl)-8-(4-morpholinylmethyl)-6-oxo-6H-pyrrolo[3,2,1-ij]quinoline-5-carboxamide

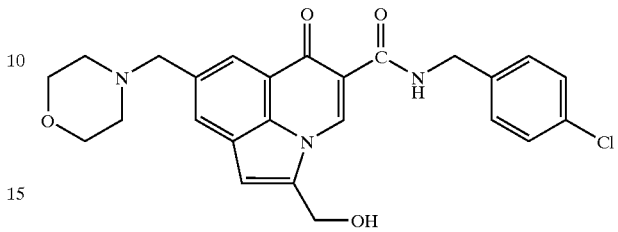

To a solution of N-(4-chlorobenzyl)-4-hydroxy-8-iodo-6-(4-morpholinylmethyl)-3-quinolinecarboxamide (0.15 g), $PdCl_2(PPh_3)_2$ (0.0098 g) and CuI (0.0027 g) in diethylamine (5.2 mL) and $CH_2Cl_2$ (5 mL) is added propargyl alcohol (0.016 mL). The reaction is stirred at room temperature overnight, then concentrated. The crude residue is partitioned between $CH_2Cl_2$ and water. The aqueous layer is extracted with $CH_2Cl_2$ (3x). The combined organic layers are dried over $Na_2SO_4$ and condensed. The crude product is adsorbed onto silica and chromatographed (Biotage flash 40S, gradient from $CH_2Cl_2$ to 2.5% $MeOH/CH_2Cl_2$). Product containing fractions are combined and concentrated. The resulting solid is triturated with $CH_2Cl_2$/hexanes, filtered and dried to yield 0.029 g (23%) of N-(4-chlorobenzyl)-2-(hydroxymethyl)-8-(4-morpholinylmethyl)-6-oxo-6H-pyrrolo[3,2,1-ij]quinoline-5-carboxamide, m.p. 210–212° C.

$^1$H NMR (300 MHz, DMSO-$d_6$) δ 10.15, 9.29, 8.05, 8.01, 7.40, 7.05, 5.79, 4.91, 4.59, 3.71, 3.58, 2.40; IR (drift) 3387, 1662, 1629, 1592, 1569, 1542, 1491, 1350, 1308, 1245, 1222, 1113, 1015, 881, 807 cm$^{-1}$; MS (EI) m/z 465 (M+), 465, 380, 298, 240, 239, 213, 140, 91, 86, 32; HRMS (EI) calcd for $C_{25}H_{24}ClN_3O_4$ 465.1455, found 465.1452.

Example 4

N-(4-Chlorobenzyl)-2-(2-hydroxyethyl)-8-(4-morpholinylmethyl)-6-oxo-6H-pyrrolo[3,2,1-ij]quinoline-5-carboxamide

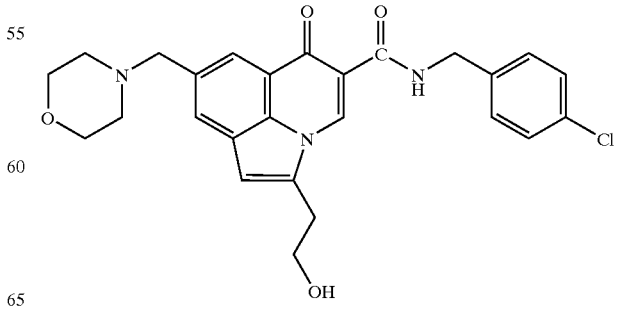

To a suspension of N-(4-chlorobenzyl)-4-hydroxy-8-iodo-6-(4-morpholinylmethyl)-3-quinolinecarboxamide (581.4 mg) and PdCl$_2$(PPh$_3$)$_2$ (37.9 mg) in Et$_3$N (20 mL) is added CuI (10.3 mg) and 3-butyn-1-ol (0.082 mL). The reaction is stirred at room temperature for 2 days under N$_2$. After 2 days the solvent evaporates. The resulting solid is dissolved in CH$_2$Cl$_2$ and partitioned against H$_2$O. The aqueous layer is extracted with CH$_2$Cl$_2$ (2×). The combined organic layers are washed with brine (1×), dried over Na$_2$SO$_4$, filtered, and condensed. The crude solid is adsorbed onto silica and chromatographed (Biotage flash 40S, gradient from CH$_2$Cl$_2$ to 3% MeOH in CH$_2$Cl$_2$). Product-containing fractions are combined and concentrated to yield a creme solid. The solid is recrystallized from hot acetonitrile to afford 290 mg (56%) of N-(4-chlorobenzyl)-2-(2-hydroxyethyl)-8-(4-morpholinylmethyl)-6-oxo-6H-pyrrolo[3,2,1-ij]quinoline-5-carboxamide as an off-white solid, m.p. 169–172° C.

$^1$H NMR (300 MHz, DMSO-d$_6$) δ 10.17, 9.23, 7.99, 7.96, 7.40, 6.93, 5.01, 4.59, 3.78, 3.70, 3.58, 3.19, 2.40; IR (diffuse reflectance) 1662, 1628, 1591, 1543, 1491, 1351, 1305, 1246, 1222, 1114, 1059, 1014, 879, 805, 655 cm$^{-1}$; MS (ESI) for m/z 479.9 (M+H)$^+$, 477.9 (M−H)$^-$; Anal. calcd for C$_{26}$H$_{26}$ClN$_3$O$_4$: C, 65.06; H, 5.46; N, 8.76, found: C, 65.08; H, 5.50; N, 8.66.

By the method of Example 4, using the appropriate starting materials and heating the reactions to 80° C. for 18 hrs, the following compounds are prepared:

Example 5

N-(4-Chlorobenzyl)-2-(2-morpholin-4-ylethyl)-8-(4-morpholinylmethyl)-6-oxo-6H-pyrrolo[3,2,1-ij]quinoline-5-carboxamide

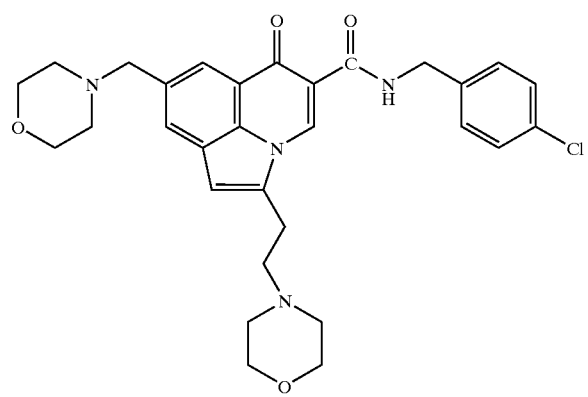

$^1$H NMR (300 MHz, DMSO-d$_6$) δ 10.15, 9.28, 8.00, 7.40, 6.96, 4.60, 3.70, 3.60, 3.24, 3.10, 2.71, 2.49, 2.40; MS (ESI) for m/z 549.1, 551.1, 552.1(M+H)$^+$.

Example 6

N-(4-Chlorobenzyl)-2-[2-(diethylamino)ethyl]-8-(4-morpholinylmethyl)-6-oxo-6H-pyrrolo[3,2,1-ij]quinoline-5-carboxamide

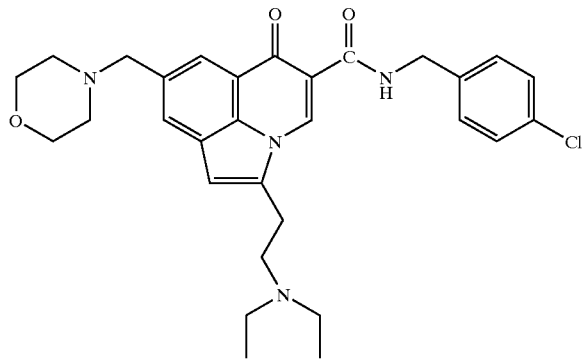

$^1$H NMR (300 MHz, DMSO-d$_6$) δ 10.16, 9.23, 7.99, 7.96, 7.40, 6.93, 4.59, 3.70, 3.58, 3.16, 2.80, 2.56, 2.40, 0.93; MS (ESI) for m/z 536.1(M+H)$^+$.

Example 7

N-(4-Chlorobenzyl)-2-[2-(4-methylpiperazin-1-yl)ethyl]-8-(morpholin-4-ylmethyl)-6-oxo-6H-pyrrolo[3,2,1-ij]quinoline-5-carboxamide

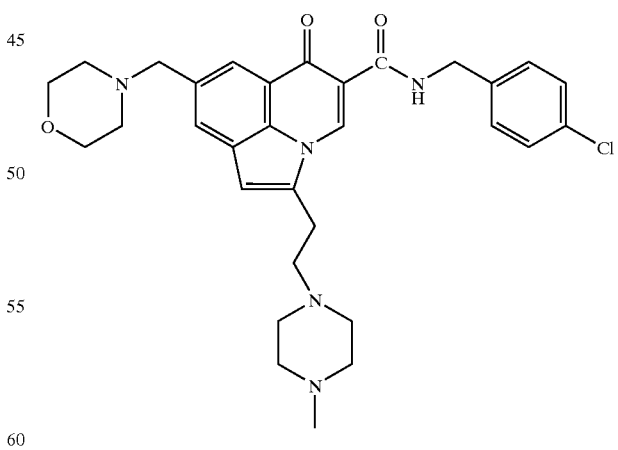

$^1$H NMR (300 MHz, DMSO-d$_6$) δ 10.21, 9.35, 8.00, 7.98, 7.40, 6.95, 4.60, 3.72, 3.58, 3.24, 2.65, 2.54, 2.42; MS (ESI) for m/z 562.3(M+H)$^+$.

Example 8

N-(4-Chlorobenzyl)-2-[2-(2-ethylpiperidin-1-yl)ethyl]-8-(morpholin-4-ylmethyl)-6-oxo-6H-pyrrolo[3,2,1-ij]quinoline-5-carboxamide

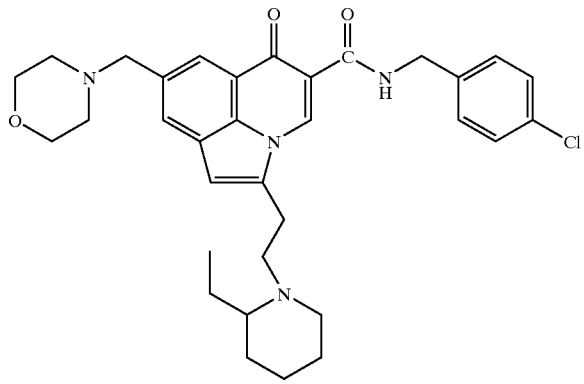

$^1$H NMR (300 MHz, DMSO-d$_6$) δ 10.17, 9.26, 8.00, 7.98, 7.40, 6.98, 4.57, 3.72, 3.17, 2.55, 2.38, 1.65, 1.24, 0.75; MS (ESI) for m/z 575.1, 577.1, 578.1 (M+H)$^+$.

Example 9

N-(4-Chlorobenzyl)-2-[3-(4-methylpiperazin-1-yl)propyl]-8-(morpholin-4-ylmethyl)-6-oxo-6H-pyrrolo[3,2,1-ij]quinoline-5-carboxamide

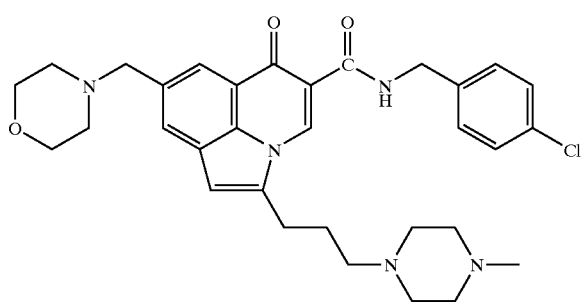

$^1$H NMR (300 MHz, DMSO-d$_6$) δ 10.17, 9.15, 7.98, 7.95, 7.40, 6.89, 4.60, 3.70, 3.57, 3.17, 3.07, 2.40, 1.90; MS (ESI) for m/z 576.4(M+H)$^+$.

Example 10

N-(4-Chlorobenzyl)-8-(morpholin-4-ylmethyl)-6-oxo-2-(2-piperidin-1-ylethyl)-6H-pyrrolo[3,2,1-ij]quinoline-5-carboxamide

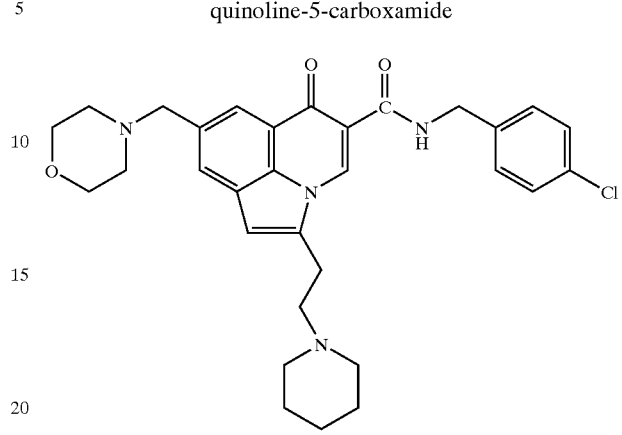

$^1$H NMR (300 MHz, DMSO-d$_6$) δ 10.17, 9.24, 8.00, 7.97, 7.40, 6.94, 4.60, 3.70, 3.64, is 3.26, 2.62, 2.39, 1.55; MS (ESI) for m/z 547.6(M+H)$^+$.

Example 11

N-(4-Chlorobenzyl)-8-(morpholin-4-ylmethyl)-2-(3-morpholin-4-ylpropyl)-6-oxo-6H-pyrrolo[3,2,1-ij]quinoline-5-carboxamide

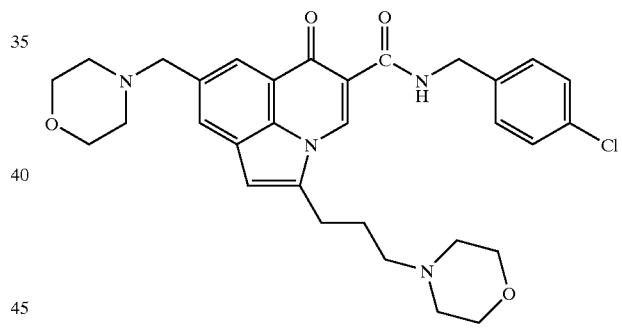

$^1$H NMR (300 MHz, DMSO-d$_6$) δ 10.16, 9.17, 7.98, 7.95, 7.39, 6.90, 4.60, 3.70, 3.64, 3.51, 3.09, 2.54, 2.37, 1.90; MS (ESI) for m/z 563.7(M+H)$^+$.

Preparation 13 Polymer Supported 3-butyn-1-ol sulfonate

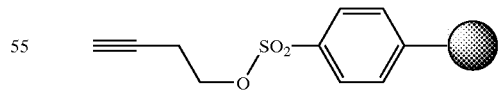

Polystyrene-Ts-Cl resin (2.125 g, 1.35 meq/g, 2.88 mmol) and 3-butyn-1-ol (654 μL) is shaken in 1:1 DCM/pyridine (14 mL) for 18 hrs. The resin is washed with DCM (3×), DMF (5×), DMF/H$_2$O (3:1, 5×), THF (3×), DCM (3×) and is dried under vacuum. The resin is used without characterization in subsequent reactions. Following this procedure, but substituting 3-butyn-1-ol with other C$_{1-12}$alkynyl alcohol, polymer supported C$_{1-12}$alkynol sulfonate can be obtained.

Preparation 14 4-But-3-ynylmorpholine

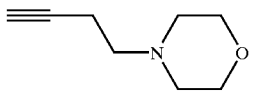

The product of Preparation 13 (600 mg) is treated with morpholine (57 μL) in acetonitrile (2 mL) at 70° C. for 18 h. The solution is filtered into a pre-tared vial and the resin is further washed with THF and DCM. The solvent is then concentrated to give crude 4-but-3-ynylmorpholine which is directly used in the following reaction: MS (ESI) for m/z 140.1 (M+H)$^+$. Following this procedure, but substituting polymer supported 3-butyn-1-ol sulfonate with other polymer supported $C_{1-12}$alkynol sulfonate; and substituting morpholine with other primary, and secondary alkylamine, compounds of formula $C_{1-12}$alkynyl-$NR_xR_x$, wherein each Rx is independently H, $C_{1-7}$alkyl, or each Rx together with the nitrogen form a het. The het is the same as defined previously. By the method of Preparation 14 and using the appropriate starting materials, the following compounds are prepared:

Preparation 15 1-But-3-ynylpiperidine

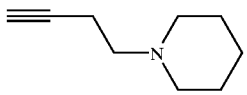

MS (ESI) for m/z 138.0(M+H)$^+$.

Preparation 16 N-But-3-ynyl-N,N-diethylamine

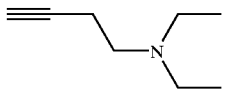

MS (ESI) for m/z 126.0(M+H)$^+$.

Preparation 17 1-But-3-ynyl-2-ethylpiperidine

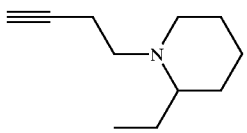

MS (ESI) for m/z 166.1 (M+H)$^+$.

Preparation 18 1-But-3-ynyl-4-methylpiperazine

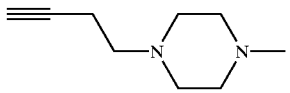

MS (ESI) for m/z 153.1 (M+H)$^+$.

By the method of Preparation 14, substituting 4-pentyn-1-ol in Preparation 13, and using the appropriate starting materials, the following compounds are prepared:

Preparation 19 4-Pent-4-ynylmorpholine

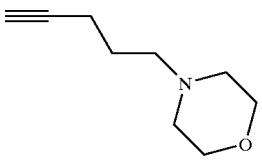

MS (ESI) for m/z 154.1 (M+H)$^+$.

Preparation 20 1-Methyl-4-pent-4-ynylpiperazine

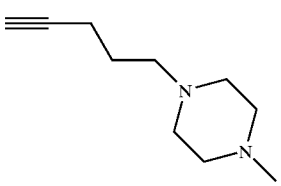

MS (ESI) for m/z 167.1 (M+H)$^+$.

Example 12

N-(4-Chlorobenzyl)-2-[(1,1-dioxido-4-thiomorpholinyl)methyl]-8-(4-morpholinylmethyl)-6-oxo-6H-pyrrolo[3,2,1-ij]quinoline-5-carboxamide

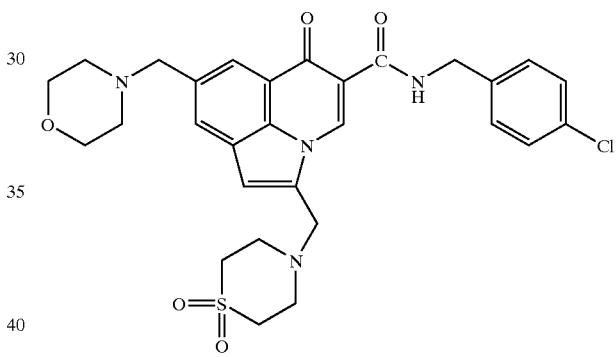

and

Example 13

N-(4-Chlorobenzyl)-2-[(1,1-dioxido-4-thiomorpholinyl)methyl]-1-iodo-8-(4-morpholinylmethyl)-6-oxo-6H-pyrrolo[3,2,1-ij]quinoline-5-carboxamide

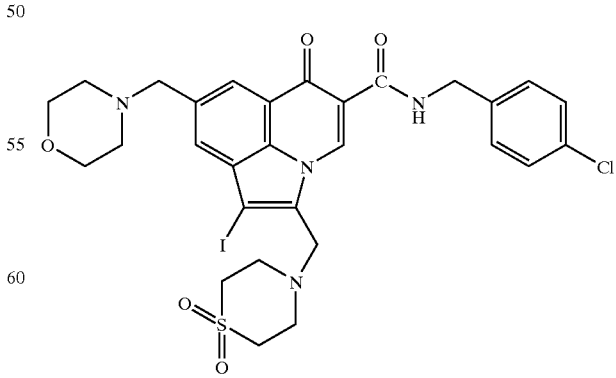

A suspension of N-(4-chlorobenzyl)-4-hydroxy-8-iodo-6-(4-morpholinylmethyl)-3-quinolinecarboxamide (300 mg), PdCl$_2$(PPh$_3$)$_2$ (39.2 mg), CuI (12.8 mg), Et$_2$NH (0.12 mL), and 4-propargylthiomorpholine-1,1-dioxide (116.2 mg) in CHCl$_3$ (5.6 mL) is stirred at room temperature for 18 days. The reaction mixture is condensed, adsorbed onto silica, and chromatographed eluting with CH$_2$Cl$_2$ to 2% MeOH in CH$_2$Cl$_2$. Fractions homogenous by TLC are combined, concentrated, and recrystallized from hot acetonitrile to afford 73.3 mg (23%) of N-(4-chlorobenzyl)-2-[(1,1-dioxido-4-thiomorpholinyl)methyl]-8-(4-morpholinylmethyl)-6-oxo-6H-pyrrolo[3,2,1-ij]quinoline-5-carboxamide as a yellow solid and 49.1 mg (12%) of N-(4-chlorobenzyl)-2-[(1,1-dioxido-4-thiomorpholinyl)methyl]-1-iodo-8-(4-morpholinylmethyl)-6-oxo-6H-pyrrolo[3,2,1-ij]quinoline-5-carboxamide as a yellow solid.

N-(4-chlorobenzyl)-2-[(1,1-dioxido-4-thiomorpholinyl)methyl]-8-(4-morpholinylmethyl)-6-oxo-6H-pyrrolo[3,2,1-ij]quinoline-5-carboxamide:

m.p. 236–239° C.; $^1$H NMR (300 MHz, DMSO-d$_6$) δ 10.15, 9.37, 8.04, 8.00, 7.40, 7.11, 4.59, 4.22, 3.70, 3.58, 3.12, 3.08, 2.08; IR (diffuse reflectance) 1667, 1639, 1588, 1550, 1532, 1493, 1331, 1320, 1291, 1273, 1130, 1122, 1115, 860, 806 cm$^{-1}$;

MS (ESI) for m/z 582.8 (M+H)$^+$, 580.8 (M−H)$^-$; Anal. Calcd for C$_{29}$H$_{31}$ClN$_4$O$_5$S: C, 59.74; H, 5.36; N, 9.61, found: C, 59.69; H, 5.34; N, 9.62.

N-(4-chlorobenzyl)-2-[(1,1-dioxido-4-thiomorpholinyl)methyl]-1-iodo-8-(4-morpholinylmethyl)-6-oxo-6H-pyrrolo[3,2,1-ij]quinoline-5-carboxamide:

m.p. 244–246° C.; $^1$H NMR (300 MHz, DMSO-d$_6$) δ 10.07, 9.35, 8.08, 7.77, 7.40, 4.59, 4.24, 3.75, 3.58, 3.12, 3.08, 2.41; IR (diffuse reflectance) 1668, 1589, 1550, 1536, 1486, 1344, 1332, 1303, 1293, 1273, 1210, 1123, 1110, 861, 809 cm$^{-1}$; MS (ESI) for m/z 708.7 (M+H)$^+$; Anal. Calcd for C$_{29}$H$_{30}$ClIN$_4$O$_5$S: C, 49.13; H, 4.26; N, 7.90, found: C, 49.14; H, 4.25; N, 8.00.

Example 14

N-(4-Chlorobenzyl)-2-(3-hydroxypropyl)-8-(4-morpholinylmethyl)-6-oxo-6H-pyrrolo[3,2,1-ij]quinoline-5-carboxamide

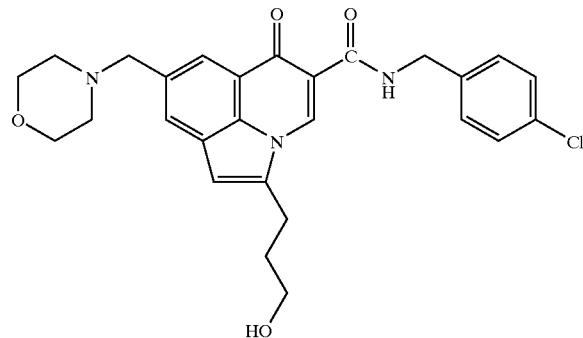

A suspension of N-(4-chlorobenzyl)-4-hydroxy-8-iodo-6-(4-morpholinylmethyl)-3-quinolinecarboxamide (800 mg), PdCl$_2$(PPh$_3$)$_2$ (104.6 mg), CuI (34.1 mg), 4-pentyn-1-ol (0.17 mL), and Et$_3$N (0.42 mL) in CHCl$_3$ (14.9 mL) is stirred at room temperature overnight. Reaction condensed to remove CHCl$_3$. The solvent is replaced with EtOH (15 mL) and additional Et$_3$N (0.38 mL) is added to the reaction mixture. N$_2$ is passed over the surface and the reaction is heated at 76° C. for 6 h, then allowed to cool to room temperature. Reaction mixture is condensed, adsorbed onto silica, and chromatographed eluting with 1% MeOH in CH$_2$Cl$_2$ to 3% MeOH in CH$_2$Cl$_2$. Product-containing fractions are combined, condensed, and recrystallized from hot acetonitrile to afford 408.9 mg (56%) of N-(4-chlorobenzyl)-2-(3-hydroxypropyl)-8-(4-morpholinylmethyl)-6-oxo-6H-pyrrolo[3,2,1-ij]quinoline-5-carboxamide as a yellow solid.

m.p. 171–174° C.; $^1$H NMR (300 MHz, DMSO-d$_6$) δ 10.16, 9.13, 7.98, 7.94, 7.40, 6.88, 4.68, 4.59, 3.70, 3.55, 3.09, 2.40, 1.90; IR (diffuse reflectance) 3465, 1661, 1633, 1580, 1570, 1549, 1544, 1492, 1322, 1276, 1249, 1114, 809, 798, 698 cm$^{-1}$;

HRMS (FAB) calcd for C$_{27}$H$_{28}$ClN$_3$O$_4$+H, 494.1846, found 494.1845; Anal. Calcd for C$_{27}$H$_{28}$ClN$_3$O$_4$: C, 65.65; H, 5.71; N, 8.51, found: C, 65.28; H, 5.72; N, 8.47.

Example 15

2-{[(Aminocarbonyl)amino]methyl}-N-(4-chlorobenzyl)-8-(4-morpholinylmethyl)-6-oxo-6H-pyrrolo[3,2,1-ij]quinoline-5-carboxamide

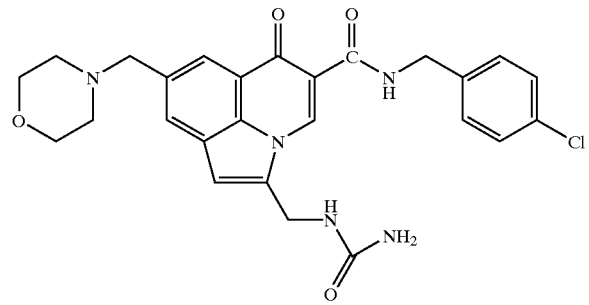

A solution of N-(4-chlorobenzyl)-4-hydroxy-8-iodo-6-(4-morpholinylmethyl)-3-quinolinecarboxamide (300 mg), PdCl$_2$(PPh$_3$)$_2$ (19.7 mg), CuI (5.3 mg), Et$_3$N (10.4 mL), and prop-2-ynylurea (60.3 mg) is stirred at room temperature overnight. Distilled CH$_2$Cl$_2$ (10.4 mL) and additional PdCl$_2$(PPh$_3$)$_2$ (19.7 mg) and CuI (5.3 mg) are added. The reaction is stirred at room temperature overnight. The reaction mixture is condensed, adsorbed onto silica, and chromatographed eluting with 2% MeOH in CH$_2$Cl$_2$ to 6.5% MeOH in CH$_2$Cl$_2$. Product containing fractions are combined and condensed to afford a mixture of cyclized and uncyclized materials. To a scintillation vial is added the mixture, EtOH (4 mL), Et$_3$N (0.1 mL), and CuI (~1 mg). The suspension is heated at 70° C. overnight. The reaction mixture is condensed, adsorbed onto silica, and chromatographed eluting with 6% MeOH in CH$_2$Cl$_2$ then 7% MeOH in CH$_2$Cl$_2$. Product-containing fractions are combined and condensed to afford a solid. The solid is suspended in CH$_2$CT$_2$/hexanes and filtered to afford 19.7 mg (7%) of 2-{[(aminocarbonyl)amino]methyl}-N-(4-chlorobenzyl)-8-(4-morpholinylmethyl)-6-oxo-6H-pyrrolo[3,2,1-ij]quinoline-5-carboxamide as a white solid.

m.p. 250–252° C.; $^1$H NMR (300 MHz, DMSO-d$_6$) δ 10.13, 9.34, 8.04, 7.99, 7.40, 6.97, 6.66, 5.70, 4.61, 3.71, 3.58, 2.40; HRMS (FAB) calcd for C$_{26}$H$_{26}$ClN$_5$O$_4$+H$_1$ 508.1751, found 508.1752; Anal. Calcd for C$_{26}$H$_{26}$ClN$_5$O$_4$: C, 61.48; H, 5.16; N, 13.79, found: C, 60.01; H, 5.22; N, 13.39.

Example 16

N-(4-Chlorobenzyl)-2-[(1R)-1-hydroxyethyl]-8-(4-morpholinylmethyl)-6-oxo-6H-pyrrolo[3,2,1-ij]quinoline-5-carboxamide

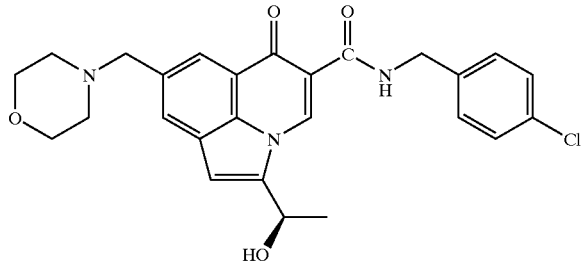

To a suspension of N-(4-chlorobenzyl)-4-hydroxy-8-iodo-6-(4-morpholinylmethyl)-3-quinolinecarboxamide (300 mg), $PdCl_2(PPh_3)_2$ (39.2 mg), CuI (12.8 mg), and $Et_3N$ (0.16 mL) in $CHCl_3$ (5.6 mL) is added (R)-(+)-3-butyn-2-ol (0.053 mL). The reaction is stirred at room temperature for 2 days. The reaction is condensed to remove $CHCl_3$. The solvent is replaced with EtOH (5.6 mL) and additional $Et_3N$ (0.16 mL) is added to the reaction mixture. $N_2$ is passed over the surface and the reaction is heated at 60° C. overnight, then allowed to cool to room temperature. The reaction mixture is condensed, adsorbed onto silica, and chromatographed eluting with 1% MeOH in $CH_2Cl_2$ to 3% MeOH in $CH_2Cl_2$. Product-containing fractions are combined, condensed, and recrystallized from hot acetonitrile to afford 33.8 mg (13%) of N-(4-chlorobenzyl)-2-[(1R)-1-hydroxyethyl]-8-(4-morpholinylmethyl)-6-oxo-6H-pyrrolo[3,2,1-ij]quinoline-5-carboxamide as a tan solid. m.p. 155–159° C.; $^1$H NMR (300 MHz, DMSO-$d_6$) δ 10.16, 9.42, 8.05, 8.01, 7.40, 7.02, 5.90, 5.26, 4.59, 3.71, 3.58, 2.40, 1.61; IR (diffuse reflectance) 1662, 1629, 1592, 1569, 1541, 1490, 1349, 1294, 1279, 1271, 1245, 1229, 1114, 879, 807 $cm^{-1}$;

MS (ESI) for m/z 480.0 $(M+H)^+$; Anal. Calcd for $C_{26}H_{26}ClN_3O_4$: C, 65.06; H, 5.46; N, 8.76; found: C, 64.95; H, 5.57; N, 8.60.

Preparation 21 4-(4-Nitrobenzyl)morpholine

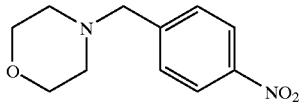

To a flask containing 4-nitrobenzyl bromide (21.6 g) in dry acetone (100 mL) is added potassium carbonate (34.5 g) and morpholine (10 mL). The mixture is heated to reflux overnight under a drying tube. The reaction is partitioned between ethyl acetate and water and separated. The basic aqueous layer is extracted with two additional portions of ethyl acetate. The combined organic layers are washed with brine, dried, and concentrated under reduced pressure to afford 21.3 g of the title compound as a solid.

Physical characteristics are as follows:

Mp 75–79° C.; $^1$H NMR (300 MHz, $CDCl_3$) 8.2, 7.6, 3.7, 3.6, 2.4.

Preparation 22 4-(4-Aminobenzyl)morpholine

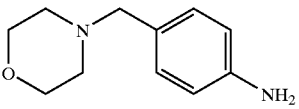

To a solution of 4-(4-nitrobenzyl)morpholine from Preparation 21 (0.89 g) in ethyl acetate (10 mL) is added 5% platinum on carbon (0.04 g). The reaction is shaken under 30 psi of hydrogen gas for 1 hour. The mixture is filtered with ethyl acetate washes. The filtrate is concentrated under reduced pressure to afford 0.71 g of the title compound as a yellow solid.

Physical characteristics are as follows:

$^1$H NMR (300 MHz, $CDCl_3$) 7.1, 6.6, 3.7, 3.6, 3.4, 2.4; MS (ESI) m/z 193 $(M+H^+)$.

Preparation 23 2-iodo-4-(4-morpholinylmethyl)aniline

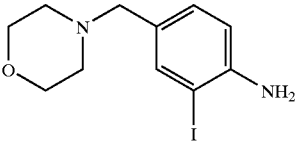

To a flask containing 4-(4-aminobenzyl)morpholine from Preparation 22 (4.8 g) is added dichloromethane (100 mL) and acetic acid (25 mL). The solution is treated dropwise with a solution of iodine monochloride (5.67 g) in dichloromethane (100 mL) over 1 hour. After 2 additional hours of stirring, the reaction mixture is carefully poured into a mixture of saturated aqueous sodium carbonate (300 mL), sodium thiosulfate (25 g) and water (100 mL). The residue remaining in the reaction flask is dissolved in dichloromethane containing a small amount of methanol and the resulting solution is added to the quench mixture. The mixture is vigorously stirred and then separated. The aqueous phase is extracted with dichloromethane (3×100 mL). The combined organic layers are washed with water (100 mL), brine (100 mL), dried over sodium sulfate, and concentrated under reduced pressure. The residue is flash column chromatographed on silica eluting with 2% to 6% methanol in dichloromethane. The product-containing fractions are combined and evaporated to afford 6.33 g of the title compound.

Physical characteristics are as follows:

$^1$H NMR (300 MHz, $CDCl_3$) 7.6, 7.1, 6.7, 4.1, 3.7, 3.4, 2.4; MS (ESI) m/z 319 $(M+H^+)$.

Preparation 24 Diethyl 2-{[2-iodo-4-(4-morpholinylmethyl)anilino]methylene}malonate

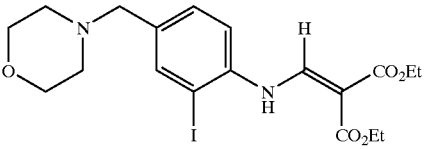

To a flask containing 2-iodo-4-(4-morpholinylmethyl)aniline (4.33 g) from Preparation 23 is added diethyl ethoxymethylenemalonate (3.0 mL). The solution is degassed briefly under reduced pressure and then heated to 165° C. for 2 hours under an argon atmosphere. The reaction is cooled to room temperature and diluted with toluene (10 mL). The mixture is gently warmed to afford a solution which is slowly treated with hot hexanes (30 mL). The resulting suspension is cooled to room temperature, then placed in a freezer. The resulting solid is collected, washed with hexanes, and dried to afford the title compound.

Physical characteristics are as follows:

$^1$H NMR (300 MHz, CDCl$_3$) 11.1, 8.4, 7.8, 7.4, 7.2, 4.4, 4.3, 3.7, 3.4, 2.5, 1.4, 1.3.

Preparation 25 Ethyl 4-hydroxy-8-iodo-6-(4-morpholinylmethyl)-3-quinolinecarboxylate

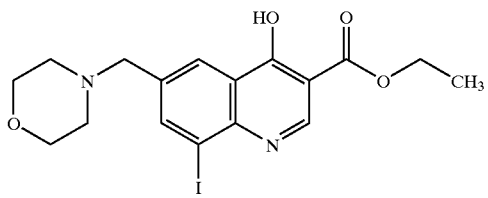

To a flame-dried, 3-neck round bottom flask equipped with an overhead stirrer is added phosphorous pentoxide (4.82 g) under a flow of argon gas. The flask is charged with methanesulfonic acid (35 mL) heated to 90° C. After 1 hour, the resulting solution is treated with diethyl 2-{[2-iodo-4-(4-morpholinylmethyl)anilino]methylene}malonate from Preparation 24 (6.12 g) as a solution in dichloromethane (25 mL). The dichloromethane is removed by the argon flow. After 3 hours, the reaction mixture is cooled to room temperature, poured into an ice-cold beaker and slowly quenched with ice until exothermic addition subsides. The swirled mixture is then treated with aqueous sodium hydroxide (50%, ~30 mL) dropwise to afford a basic aqueous phase. Ice is also added during sodium hydroxide addition to control the exotherm. The mixture is treated with dichloromethane (100 mL) and the layers are separated. The basic aqueous layer is extracted with four additional portions of dichloromethane. The combined organic layers are washed with brine, dried over sodium sulfate and concentrated under reduced pressure. The residue is chromatographed on silica eluting with 2% to 8% methanol in dichloromethane to afford 3.12 g of the title compound as a solid.

Physical characteristics are as follows:

$^1$H NMR (300 MHz, CDCl$_3$) 12.3, 9.2, 8.4, 8.2, 4.5, 3.8, 3.6, 2.5, 1.5; MS (ESI) m/z 443 (M+H$^+$).

Preparation 26 N-(4-Chlorobenzyl)-4-hydroxy-8-iodo-6-(4-morpholinylmethyl)-3-quinolinecarboxamide

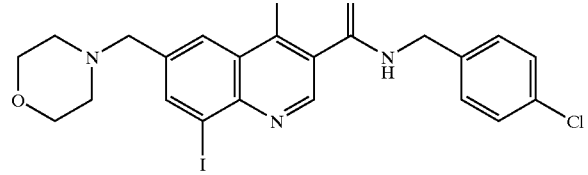

To a flask containing ethyl 4-hydroxy-8-iodo-6-(4-morpholinylmethyl)-3-quinolinecarboxylate of Preparation 25 (3.11 g) is added 4-chlorobenzylamine (8.0 mL). The mixture is degassed under reduced pressure. The mixture is placed under an argon atmosphere and is heated at 190° C. for 3 h. The reaction is cooled to room temperature. The excess benzylamine is removed by high vacuum distillation. The residue is crystallized from acetonitrile:methanol (1:1, 800 mL) to yield 3.08 g of the title compound as a white solid.

$^1$H NMR (300 MHz, DMSO-d$_6$) δ 11.6, 10.3, 8.7, 8.2, 8.2, 7.4, 4.6, 3.6, 2.4; OAMS ESI+ 538 (M+H$^+$).

Example 17

N-(4-Chlorobenzyl)-2-(methoxymethyl)-8-(4-morpholinylmethyl)-6-oxo-6H-pyrrolo[3,2,1-ij]quinoline-5-carboxamide

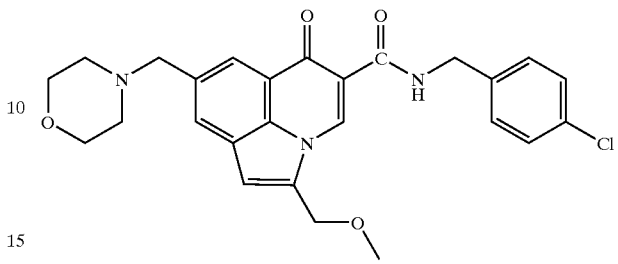

To a flame-dried flask under a nitrogen atmosphere is added N-(4-chlorobenzyl)-4-hydroxy-8-iodo-6-(4-morpholinylmethyl)-3-quinolinecarboxamide (269 mg) of Preparation 26, PdCl$_2$(PPh$_3$)$_2$ (18 mg), and CuI (10 mg). The flask is back-filled with nitrogen gas and charged with dichloromethane (10 mL), Et$_3$N (0.14 mL), and methyl propargyl ether (0.046 mL). The reaction is stirred at room temperature for 4 days. The reaction mixture is diluted with dichloromethane and partitioned against dilute aqueous sodium carbonate. The aqueous phase is extracted with two portions of dichloromethane. The combined organic layers are washed with brine, dried over sodium sulfate and concentrated under reduced pressure. The residue is flash column chromatographed on silica gel eluting with 1% to 4% methanol in dichloromethane. The product containing fractions are combined and concentrated under reduced pressure to give a yellow solid which is crystallized from toluene to afford 0.13 g of the title compound as tan needles.

m.p. 157–159° C.; $^1$H NMR (300 MHz, DMSO-d$_6$) δ 10.1, 9.2, 8.1, 8.0, 7.4, 7.2, 4.9, 4.6, 3.7, 3.6, 3.4, 2.4; MS (ESI) m/z 480 (M+H$^+$); Anal. calcd for C$_{26}$H$_{26}$ClN$_3$O$_4$: C, 65.06; H, 5.46; N, 8.76; Cl, 7.39, found: C, 64.90; H, 5.55; N, 8.52.

Example 18

N-(4-Chlorobenzyl)-2-[(ethylsulfanyl)methyl]-8-(4-morpholinylmethyl)-6-oxo-6H-pyrrolo[3,2,1-ij]quinoline-5-carboxamide

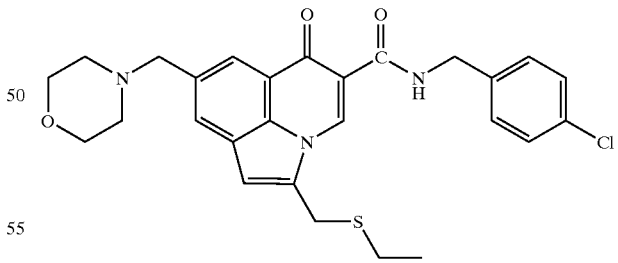

To a flame-dried flask under a nitrogen atmosphere is added N-(4-chlorobenzyl)-4-hydroxy-8-iodo-6-(4-morpholinylmethyl)-3-quinolinecarboxamide (269 mg) of Preparation 26, PdCl$_2$(PPh$_3$)$_2$ (35 mg), and CuI (12 mg). The flask is back-filled with nitrogen gas and charged with dichloromethane (5 mL), Et$_3$N (0.15 mL), and propargyl ethyl sulfide (0.066 mL). The reaction is stirred at room temperature for 4 days. The reaction mixture is diluted with dichloromethane and partitioned against dilute aqueous sodium bicarbonate. The aqueous phase is extracted with two portions of dichloromethane. The combined organic layers are washed with brine, dried over sodium sulfate and concentrated under reduced pressure. The residue is chromatographed on silica gel eluting with 1% to 2% methanol in ethyl acetate. Product containing fractions are combined and condensed to afford a mixture of cyclized and uncyclized materials. To a flask is added the mixture, EtOH (2 mL), and Et$_3$N (0.1 mL). The suspension is heated at 75° C. overnight tightly capped. The reaction mixture is cooled to room temperature, concentrated under reduced pressure, adsorbed onto silica, and flash column chromatographed eluting with 2% to 4% methanol in ethyl acetate. Product-containing fractions are combined and concentrated under reduced pressure to afford a solid. The solid is crystallized from acetonitrile to give 0.12 g of the title compound as light tan product.

m.p. 177–178° C.; $^1$H NMR (300 MHz, DMSO-d$_6$) δ 10.1, 9.3, 8.0, 8.0, 7.4, 7.0, 4.6, 4.3, 3.7, 3.6, 2.5, 2.4, 1.2; HRMS (FAB) calcd for C$_{27}$H$_{29}$ClN$_3$O$_3$S+H$_1$ 510.1618, found 510.1617; Anal. Calcd for C$_{27}$H$_{27}$ClN$_3$O$_3$S: C, 63.58; H, 5.53; N, 8.24; found: C, 63.45; H, 5.58; N, 8.19.

Example 19

N-(4-Chlorobenzyl)-8-(4-morpholinylmethyl)-6-oxo-2-[(phenylsulfanyl)methyl]-6H-pyrrolo[3,2,1-ij]quinoline-5-carboxamide

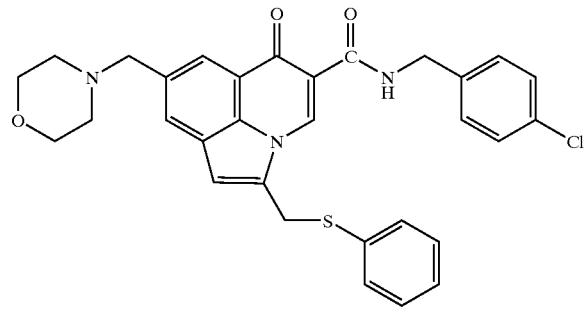

To a flame-dried flask under a nitrogen atmosphere is added N-(4-chlorobenzyl)-4-hydroxy-8-iodo-6-(4-morpholinylmethyl)-3-quinolinecarboxamide (269 mg) of Preparation 26, PdCl$_2$(PPh$_3$)$_2$ (35 mg), and CuI (12 mg). The flask is back-filled with nitrogen gas and charged with dichloromethane (5 mL), Et$_3$N (0.15 mL), and phenyl propargyl sulfide (0.082 mL). The reaction is stirred at room temperature for 7 days. The reaction mixture is diluted with dichloromethane and partitioned against dilute aqueous sodium bicarbonate. The aqueous phase is extracted with two portions of dichloromethane. The combined organic layers are washed with brine, dried over sodium sulfate and concentrated under reduced pressure. The residue is adsorbed onto silica and flash column chromatographed eluting with 1% to 3% methanol in ethyl acetate. Product containing fractions are combined and condensed to afford a mixture of cyclized and uncyclized materials. To a flask is added the mixture, EtOH (2 mL), and Et$_3$N (0.12 mL). The suspension is heated at 75° C. overnight tightly capped. The reaction mixture is cooled to room temperature, concentrated under reduced pressure, adsorbed onto silica, and flash column chromatographed eluting with 1% to 4% methanol in ethyl acetate. Product-containing fractions are combined and concentrated under reduced pressure to afford a solid. The solid is crystallized from acetonitrile to give 0.16 g of the title compound as light tan product.

m.p. 173–175° C.; $^1$H NMR (300 MHz, DMSO-d$_6$) δ 10.2, 9.4, 8.0, 7.4, 7.3, 7.2, 7.0, 4.9, 4.6, 3.7, 3.6, 2.4; HRMS (FAB) calcd for C$_{31}$H$_{28}$ClN$_3$O$_3$S+H 558.1618, found 558.1622; Anal. calcd for C$_{31}$H$_{28}$ClN$_3$O$_3$S: C, 66.71; H, 5.06; N, 7.53, found: C, 66.35; H, 5.10; N, 7.43.

Example 20

N-(4-Chlorobenzyl)-2-[(methylamino)methyl]-8-(4-morpholinylmethyl)-6-oxo-6H-pyrrolo[3,2,1-ij]quinoline-5-carboxamide

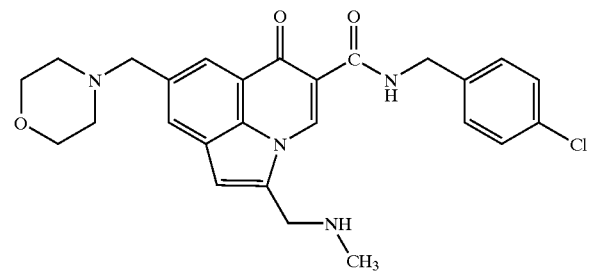

To a flame-dried flask under a nitrogen atmosphere is added N-(4-chlorobenzyl)-4-hydroxy-8-iodo-6-(4-morpholinylmethyl)-3-quinolinecarboxamide (269 mg) of Preparation 26, PdCl$_2$(PPh$_3$)$_2$ (35 mg), and CuI (12 mg). The flask is back-filled with nitrogen gas and charged with dichloromethane (5 mL), Et$_3$N (0.15 mL), and N-methylpropargylamine (0.055 mL). The reaction is stirred at room temperature for 10 days. The reaction is concentrated under reduced pressure, treated with ethanol (5 mL) and heated to 70° C. for 2 days. The reaction is cooled to room temperature and concentrated under reduced pressure. The residue is adsorbed onto silica and flash column chromatographed eluting with 2% to 10% methanol in dichloromethane. Product-containing fractions are combined and concentrated under reduced pressure to afford a solid which is crystallized from acetonitrile. The crystals are treated with hydrochloric acid (2 mL, 4N in dioxane). The suspension is diluted with methanol and concentrated under reduced pressure. The residue is triturated with small volumes of methanol-toluene, methanol-ether, toluene, and ether. The solid is treated with dichloromethane and partitioned against saturated aqueous sodium carbonate. The basic aqueous layer is extracted with two additional portions of dichloromethane. The combined organic layers are washed with brine, dried over sodium sulfate and concentrated under reduced pressure to afford 0.09 g of the title compound as an off-white solid.

$^1$H NMR (300 MHz, DMSO-d$_6$) δ 10.2, 9.4, 8.0, 8.0, 7.4, 7.0, 4.6, 4.0, 3.7, 3.6, 2.4, 2.3.

Example 21

N-(4-Chlorobenzyl)-2-[(dimethylamino)methyl]-8-(4-morpholinylmethyl)-6-oxo-6H-pyrrolo[3,2,1-ij]quinoline-5-carboxamide

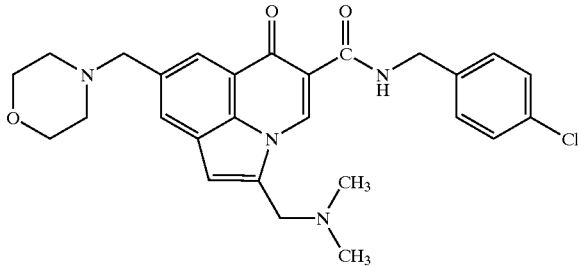

To a flame-dried flask under a nitrogen atmosphere is added N-(4-chlorobenzyl)-4-hydroxy-8-iodo-6-(4-morpholinylmethyl)-3-quinolinecarboxamide (269 mg) of Preparation 26, PdCl$_2$(PPh$_3$)$_2$ (35 mg), and CuI (12 mg). The flask is back-filled with nitrogen gas and charged with dichloromethane (5 mL), Et$_3$N (0.15 mL), 1-dimethylamino-2-propyne (0.070 mL). The reaction is stirred at room temperature for 10 days. The reaction is concentrated under reduced pressure, treated with ethanol (5 mL) and heated to 70° C. for 2 days. The reaction is cooled to room temperature and concentrated under reduced pressure. The residue is adsorbed onto silica and flash column chromatographed eluting with 1% to 4% methanol in dichloromethane. Product-containing fractions are combined and concentrated under reduced pressure to afford a solid which is crystallized from acetonitrile. The crystals are treated with hydrochloric acid (2 mL, 4N in dioxane). The suspension is diluted with methanol and concentrated under reduced pressure. The residue is triturated with small volumes of methanol-toluene, toluene, methanol-ether and ether. The solid is treated with dichloromethane and partitioned against saturated aqueous sodium carbonate. The basic aqueous layer is extracted with two additional portions of dichloromethane. The combined organic layers are washed with brine, dried over sodium sulfate and concentrated under reduced pressure to afford 0.06 g of the title compound as a tan solid.

$^1$H NMR (300 MHz, DMSO-d$_6$) δ 10.2, 9.4, 8.0, 8.0, 7.4, 7.0, 4.6, 4.0, 3.9, 3.7, 3.6, 2.4, 2.2.

Example 22

N-(4-Chlorobenzyl)-2-(2-hydroxyethyl)-6-oxo-6H-pyrrolo[3,2,1-ij]quinoline-5-carboxamide

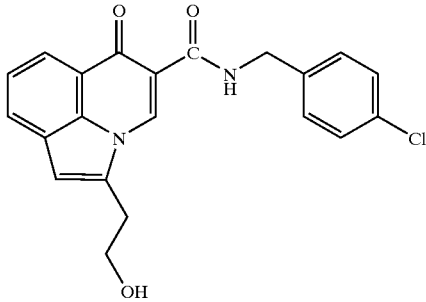

A solution of N-(4-chlorobenzyl)-4-hydroxy-8-iodo-3-quinolinecarboxamide (0.28 g), CuI (0.034 g), PdCl$_2$(PPh$_3$)$_2$ (0.012 g), and 3-butyn-1-ol (0.070 mL) in 15 mL Et$_2$NH is stirred at room temperature for 2 days. The solid in the reaction mixture is filtered and rinsed with hexanes. The filtrate is partitioned between EtOAc and H$_2$O. The aqueous layer is extracted with EtOAc (3×). Organics are combined, dried over Na$_2$SO$_4$, filtered, and concentrated. The residue is dried on high vacuum and then combined with the filtered solid, adsorbed onto silica and chromatographed (gradient from CH$_2$Cl$_2$ to 2.5% MeOH in CH$_2$Cl$_2$). Product-containing fractions are combined and condensed to afford a mixture of cyclized and uncyclized materials. A suspension of the mixture and CuT (0.037 g) in 20 mL 7:3 MeOH:Et$_3$N is heated at 70° C. for 5 h, then allowed to cool to room temperature. The reaction is partitioned between EtOAc and H$_2$O, and filtered. The aqueous layer is extracted with EtOAc (2×) and CH$_2$Cl$_2$ (1×). Organics are combined, dried over Na$_2$SO$_4$, filtered and concentrated to afford a residue. The residue is sonicated under CH$_2$Cl$_2$ and hexanes are added to precipitate 0.0782 g (32%) of N-(4-chlorobenzyl)-2-(2-hydroxyethyl)-6-oxo-6H-pyrrolo[3,2,1-ij]quinoline-5-carboxamide as a tan solid.

m.p. 190–192° C.; $^1$H NMR (300 MHz, DMSO-d$_6$) δ 10.16, 9.26, 8.05, 8.04, 7.64, 7.40, 6.95, 5.01, 4.59, 3.79, 3.20; IR (diffuse reflectance) 3330, 1671, 1639, 1587, 1551, 1491, 1466, 1344, 1304, 1296, 1271, 1252, 1054, 810, 752 cm$^{-1}$; HRMS (FAB) calcd for C$_{21}$H]7ClN$_2$O$_3$+H$_{1381.1006}$, found 381.1009; Anal. Calcd for C$_{21}$H$_{17}$ClN$_2$O$_3$: C, 66.23; H, 4.50; N, 7.36, found: C, 63.15; H, 4.46; N, 6.76.

Example 23

N-(4-Chlorobenzyl)-2-(2-hydroxyethyl)-6-oxo-8-(tetrahydro-2H-pyran-4-ylmethyl)-6H-pyrrolo[3,2,1-ij]quinoline-5-carboxamide

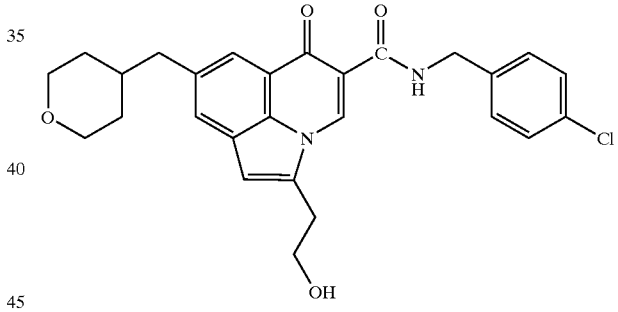

A solution of N-(4-chlorobenzyl)-4-hydroxy-8-iodo-6-(tetrahydro-2H-pyran-4-ylmethyl)-3-quinolinecarboxamide (0.16 g), PdCl$_2$(PPh$_3$)$_2$, CuI (0.018 g) and 3-butyn-1-ol (0.03 mL) in 15 mL Et$_2$NH is stirred at room temperature for 7 days. The solid in the reaction is filtered and rinsed with EtOAc. The filtrate is partitioned between EtOAc and H$_2$O. The aqueous layer is extracted with EtOAc (3×). The organic layers and the solid previously filtered are combined, concentrated, adsorbed onto silica and chromatographed (gradient from CH$_2$Cl$_2$ to 4% MeOH in CH$_2$Cl$_2$). Product-containing fractions are combined and condensed to afford 101.6 mg (71%) of N-(4-chlorobenzyl)-2-(2-hydroxyethyl)-6-oxo-8-(tetrahydro-2H-pyran-4-ylmethyl)-6H-pyrrolo[3,2,1-ij]quinoline-5-carboxamide as a tan solid.

m.p. 204–206° C.; $^1$H NMR (300 MHz, DMSO-d$_6$) δ) 10.20, 9.23, 7.88, 7.82, 7.40, 6.90, 5.01, 4.59, 3.81, 3.79, 3.22, 3.18, 2.78, 1.80, 1.46, 1.25; IR (diffuse reflectance) 3420, 2935, 2910, 2856, 1661, 1633, 1579, 1543, 1492, 1308, 1245, 1064, 851, 807, 799 cm$^{-1}$; MS (FAB) for n/z (rel. intensity) 479 (MH+, 99), 481 (40), 480 (30), 479 (99), 478 (20), 477 (20), 338 (65), 336 (22), 127 (27), 125 (49), 91 (33); HRMS (FAB) calcd for $C_{27}H_{27}ClN_2O_4+H_1$ 479.1737, found 479.1738; Anal. Calcd for $C_{27}H_{27}ClN_2O_4$: C, 67.71; H, 5.68; N, 5.85, found: C, 66.75; H, 5.69; N, 5.80.

What is claimed is:

1. A method for making an intermediate of formula $C_{2-12}$alkynyl-$NR_xR_x$ comprising t e steps of:
   (a) mixing polystyrene-Ts-Cl resin with a $C_{2-12}$alkynol, an
   (b) reacting the product of step (a) with a compound of formula $HNR_xR_x$, wherein each $R_x$ is independently H, $C_{1-7}$alkyl, or each $R_x$ taken together with the nitrogen form a het; wherein het is a four-(4), five-(5), six-(6), or seven-(7) membered saturated or unsaturated heterocyclic ring optionally having 1 or 2, additional heteroatoms selected from the group consisting of O, $SO_m$, and NX; wherein X is H, $C_{1-4}$alkyl or absent, wherein het is optionally substituted with one or more halo, $C_{1-4}$alkyl, $CF_3$, oxo or oxime; wherein m is 0, 1, or 2.

2. A compound of claim 1, wherein het is morpholine, piperdine, piperazine, thiomorpholine, azetidine, or pyrrolidine, all of which are optionally substituted by $C_{1-4}$ alkyl.

3. The method of claim 1, wherein the $C_{2-12}$alkynol is elected from 3butyn-1-ol and 4-pentyn-1-ol.

4. The method of claim 3, wherein each Rx group is ken together with the nitrogen of the $HNR_xR_x$ to form a het optionally substituted with one or more halo, $C_{1-4}$alkyl, $CF_3$, oxo or oxime.

5. The method of claim 4, wherein the $HNR_xR_x$ is selected from morpholine, piperdine, N,N-diethylamine, 2-ethylpiperdine, and 4-methyl piperazine.

6. The method of claim 1, wherein each $R_x$ group is taken together with the nitrogen of the $HNR_xR_x$ to form a het optionally substituted with one or more halo, $C_{1-4}$alkyl, $CF_3$, oxo or oxime.

7. The method of claim 6 wherein the $HNR_xR_x$ is selected from morpholine, piperdine, N,N-diethylamine, 2-ethylpiperdine, and 4-methyl piperazine.

* * * * *